(12) United States Patent
Ohashi et al.

(10) Patent No.: US 8,852,868 B2
(45) Date of Patent: Oct. 7, 2014

(54) METHOD FOR REAL-TIME NUCLEIC ACID AMPLIFICATION BY DROPLET MANIPULATION

(75) Inventors: Tetsuo Ohashi, Ibaraki (JP); Masayuki Watanabe, Muko (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/643,986

(22) PCT Filed: Feb. 2, 2011

(86) PCT No.: PCT/JP2011/052122
§ 371 (c)(1),
(2), (4) Date: Oct. 26, 2012

(87) PCT Pub. No.: WO2011/135880
PCT Pub. Date: Nov. 3, 2011

(65) Prior Publication Data
US 2013/0065236 A1 Mar. 14, 2013

(30) Foreign Application Priority Data

Apr. 28, 2010 (JP) ................................. 2010-104580

(51) Int. Cl.
*C12Q 1/68* (2006.01)

(52) U.S. Cl.
CPC ..................................... *C12Q 1/686* (2013.01)
USPC ...................................................... 435/6.12

(58) Field of Classification Search
None
See application file for complete search history.

(56) References Cited

U.S. PATENT DOCUMENTS

| | | | |
|---|---|---|---|
| 3,313,358 A | 4/1967 | Postlewaite et al. | |
| 4,683,195 A | 7/1987 | Mullis et al. | |
| 4,683,202 A | 7/1987 | Mullis | |
| 4,786,600 A | 11/1988 | Kramer et al. | |
| 4,800,159 A | 1/1989 | Mullis et al. | |
| 4,965,188 A | 10/1990 | Mullis et al. | |
| 5,234,809 A | 8/1993 | Boom et al. | |
| 5,354,688 A | 10/1994 | Francis et al. | |
| 5,409,818 A | 4/1995 | Davey et al. | |
| 5,411,876 A * | 5/1995 | Bloch et al. | 435/91.2 |
| 5,455,166 A | 10/1995 | Walker | |
| 5,494,810 A | 2/1996 | Barany et al. | |
| 6,504,226 B1 | 1/2003 | Bryant | |
| 6,864,140 B2 | 3/2005 | Bryant | |
| 6,951,722 B2 | 10/2005 | Mukai et al. | |
| 7,056,795 B2 | 6/2006 | Bryant | |
| 8,067,176 B2 * | 11/2011 | Ohashi | 435/6.12 |
| 2003/0116552 A1 | 6/2003 | Santoruvo et al. | |
| 2004/0235154 A1 * | 11/2004 | Oh et al. | 435/303.1 |
| 2005/0123950 A1 | 6/2005 | Mukai et al. | |
| 2005/0239100 A1 | 10/2005 | Mukai et al. | |
| 2007/0284360 A1 | 12/2007 | Santoruvo et al. | |

FOREIGN PATENT DOCUMENTS

| | | |
|---|---|---|
| EP | 0 368 906 B2 | 8/1999 |
| EP | 0 623 683 B1 | 9/2000 |
| JP | 2-289596 A | 11/1990 |
| JP | 2843586 B2 | 1/1999 |
| JP | 3433929 B2 | 8/2003 |
| JP | 2003-298068 A | 10/2003 |
| JP | 2004-25426 A | 1/2004 |
| JP | 2008-12490 A | 1/2008 |
| JP | 2008012490 A * | 1/2008 |
| WO | WO-88/10315 A1 | 12/1988 |
| WO | WO-00/56877 A1 | 9/2000 |

OTHER PUBLICATIONS

Okochi et al. (Droplet-based gene expression analysis using a device with magnetic force-based-droplet-handling system, Journal of Bioscience and Bioengineering, vol. 109 No. 2, 193-197, 2010).*
JP 2008012490 Decription (Translated); Jan. 2008.*
Bassam et al. (Automated "Hot Start" PCR Using Mineral oil and Paraffin Wax, BioTechniques, vol. 14, No. 1, pp. 30-34, 1993).*
Roux (Optimization and Troubleshooting in PCR, in PCR Methods and Applications, Cold Spring Harbor Laboratory, 1995).*
International Preliminary Report on Patentability for Application No. PCT/JP2011/052122 mailed Nov. 8, 2012.
International Search Report for Application No. PCT/JP2011/052122 mailed Apr. 12, 2011.
Ohashi, Tetsuo et al., "Droplet-Based Microfluidic Device with Nucleic Acid Extraction and PCR", Shimadzu Review, Mar. 2010, vol. 66, No. 3-4, pp. 209-213.

* cited by examiner

*Primary Examiner* — Christopher M Babic
*Assistant Examiner* — Aaron Priest
(74) *Attorney, Agent, or Firm* — Cheng Law Group, PLLC

(57) ABSTRACT

The present invention provides a real time nucleic acid amplification reaction method comprising performing a nucleic acid amplification reaction in a droplet present in a container. The droplet is composed of a nucleic acid amplification reaction liquid including a nucleic acid to be amplified and magnetic particles. The container holds a droplet encapsulating medium immiscible with the nucleic acid amplification reaction liquid forming the droplet, and has a transport surface having a temperature gradient. Fluorochrome is initially contained in the droplet encapsulating medium, and optionally in the droplet, at start of the nucleic acid amplification reaction. The droplet is transported together with the magnetic particles by generating and applying a magnetic field so that the droplet is placed on the transport surface at a temperature point at which the nucleic acid synthesis reaction is started and maintained, thereby controlling a temperature of the reaction liquid.

8 Claims, 4 Drawing Sheets

(a)

(b)

METHOD FOR REAL-TIME NUCLEIC ACID AMPLIFICATION BY DROPLET MANIPULATION

TECHNICAL FIELD

The present invention relates to a method for real-time nucleic acid amplification by droplet manipulation. The present invention relates to a method for real-time nucleic acid amplification used in genetic testing, especially in pathogen inspection or SNPs testing, for clinical diagnosis. The present invention relates to a method for real-time nucleic acid amplification capable of quickly and accurately detecting fluorescence obtained by a nucleic acid amplification method performed in a closed system.

BACKGROUND ART

A PCR method is a method capable of amplifying DNA or the like hundreds of thousands times by continuously performing amplification cycles each consisting of thermal denaturation, annealing with primer, and polymerase extension reaction.

A real-time PCR method is a method capable of monitoring a PCR amplified product in real time by using a fluorescent material to detect a fluorescent signal in real time by irradiating a sample with exciting light during the progress of an amplification reaction. For example, an intercalator method is a versatile and simple method using a fluorochrome such as SYBR (Registered Trade Mark) GREEN I or the like that specifically binds to double-stranded DNA.

The real-time PCR method is useful especially for analysis of trace amounts of DNA. The real-time PCR method and therefore can be used as a detection means in medical practice or researches on gene analysis to perforin monitoring of genomic DNA, including monitoring of chemical reactions.

The real-time PCR method can use a dedicated equipment or the like that is an integrated combination of a thermal cycler capable of continuously changing the temperature of a reaction liquid and a spectrofluorophotometer in order to monitor a PCR amplified product in real time. JP-A-2003-298068 (Patent Document 1) and JP-A-2004-025426 (Patent Document 2) disclose techniques relating to temperature control during amplification reaction.

The real-time PCR method allows genetic detection to be performed in a closed system, and therefore can reduce the risk of cross contamination and is excellent in quantitative performance. However, the thermal cycler used in this method is based on the principle that the temperature of a reaction liquid for PCR contained in a tube is controlled by controlling the temperature of a metal block made of aluminum or the like in which the tube containing the reaction liquid for PCR is inserted. For this reason, it is difficult to quickly change the reaction temperature, and therefore it takes 1 hour or longer to complete the reaction.

The use of a micro-chemical reaction method disclosed in JP-A-2008-012490 (Patent Document 3) makes it possible to significantly reduce the reaction time of PCR to several minutes to more than ten minutes. According to this method, a container filled with a non-aqueous liquid such as silicone oil or the like whose specific gravity is smaller than that of water can function as a thermal cycler required for PCR by sinking a droplet composed of a reaction liquid for PCR containing magnetic particles in the non-aqueous liquid and repeatedly moving the droplet to or from a heat source or vicinity thereof with the use of a magnet provided under the container. The temperature of the reaction liquid for PCR depends on the distance from the heat source to the reaction liquid for PCR and is therefore instantaneously adjusted, which makes it possible to achieve ultrahigh-speed PCR. In addition, the droplet is controlled by magnetism applied thereto from the outside of the container and therefore cross contamination affecting the accuracy of genetic detection can be minimized, which makes it possible to achieve a perfectly-closed device for gene amplification.

Patent Document 1: JP-A-2003-2980068
Patent Document 2: JP-A-2004-025426
Patent Document 3: JP-A-2008-12490

DISCLOSURE OF THE INVENTION

Problem to be Solved by the Invention

JP-A-2008-12490 discloses a method fox performing PCR in a droplet in a perfect closed system, but this method has a problem that a fluorochrome is diffused from a droplet composed of a reaction liquid for PCR into a highly-hydrophobic oil by the manipulation of transferring the droplet in the oil. More specifically, when, for example, SYBR (Registered Trade Mark) GREEN I is used as the fluorochrome, a molecule of SYBR (Registered Trade Mark) GREEN I escapes through an interface between the droplet and the oil into the oil due to hydrophobic interaction between the hydrophobic parts of the molecule itself and the oil. As a result, the concentration of the fluorochrome that binds to double-stranded DNA is significantly reduced, and therefore even when a large amount of double-stranded DNA is synthesized by PCR, it is difficult to detect fluorescence of the PCR product. Even when the concentration of the fluorochrome added to the reaction liquid is increased to solve such a problem, a PCR reaction itself cannot be performed due to inhibition by the fluorochrome.

Accordingly, it is an object of the present invention to provide a real-time nucleic acid amplification method capable of accurately detecting fluorescence based on an amplified product obtained by a nucleic acid amplification method performed in a droplet in a perfect closed system.

Means for Solving the Problem

The present inventors have found that the object of the present invention can be achieved by adding a fluorochrome to an oil when PCR is performed in a droplet in a perfect closed system so that molecules of the fluorochrome are transferred from the oil into the droplet in an amount corresponding to the number of molecules of the fluorochrome that are diffused from the droplet into the oil. This finding has led to the completion of the present invention.

The present invention includes the following inventions.

(1) A real-time nucleic acid amplification reaction method for performing a nucleic acid amplification reaction in a droplet present in a container, wherein the droplet is composed of a nucleic acid amplification reaction liquid including a nucleic acid to be amplified and magnetic particles;

the container holds a droplet encapsulating medium, and has a transport surface having a temperature gradient;

the droplet encapsulating medium is insoluble or poorly soluble in the nucleic acid amplification reaction liquid; and at least the droplet encapsulating medium out of the droplet and the droplet encapsulating medium includes a fluorochrome at start of the nucleic acid amplification reaction, the method comprising transporting the droplet together with the magnetic particles by generating a magnetic field by means for applying a magnetic field to start and maintain a nucleic acid amplification reaction so that the droplet is placed on the transport surface at a temperature point at which the nucleic acid synthesis reaction is started and maintained, thereby controlling a temperature of the nucleic acid amplification reaction liquid.

The phrase "insoluble or poorly soluble in the nucleic acid amplification reaction liquid" means that solubility in the nucleic acid amplification reaction liquid at 25° C. is about 100 ppm or less.

In the present invention, amplified nucleic acid is measured based on the fluorochrome. The measurement of amplified nucleic acid may be performed not only while the nucleic acid amplification reaction is maintained but also when the nucleic acid amplification reaction is finished.

(2) The method according to the above (1), wherein the droplet encapsulating medium includes the fluorochrome in an amount of 0.01 to 0.5 μM.

(3) The method according to the above (1) or (2), wherein the droplet includes the fluorochrome in an amount of 0 to 20 μM.

(4) The method according to any one of the above (1) to (3), wherein the droplet encapsulating medium has a gel-sol transition point lower than the temperature at which the nucleic acid, amplification reaction is started and the temperature at which the nucleic acid amplification reaction is maintained;

the droplet encapsulating medium is in a gel state at the temperature point where the droplet is present before start of the nucleic acid amplification reaction; and the droplet encapsulating medium is in a sol state at the temperature point where the droplet is present when the nucleic acid amplification reaction is started and maintained.

In the above (4), the gel-state droplet encapsulating medium allows the droplet to be fixed, and the sol-state droplet encapsulating medium allows the droplet to be transported.

(5) The method according to any one of the above (1) to (3), wherein the droplet encapsulating medium has a melting temperature lower than the temperature at which the nucleic acid amplification reaction is started and the temperature at which the nucleic acid amplification reaction is maintained;

the droplet encapsulating medium is in a solid-state before start of the nucleic acid amplification reaction, and the droplet encapsulating medium is in a melt-state when the nucleic acid amplification reaction is started and maintained.

In the above (5), the solid-state droplet encapsulating medium allows the droplet to be fixed, and the melt-state droplet encapsulating medium allows the droplet to be transported.

(6) The method according to any one of the above (1) to (5), wherein the nucleic acid to be amplified and the magnetic particles is obtained, before start of the nucleic acid amplification reaction, by bringing a nucleic acid-containing sample into contact with a nucleic acid extraction liquid in the presence of the magnetic particles in a droplet which is composed of the nucleic acid extraction liquid and is present in the container in a position different from a position in which the droplet composed of the nucleic acid amplification reaction liquid is present, thereby adsorbing an extracted nucleic acid to the magnetic particles, and wherein the magnetic particles and the extracted nucleic acid are transported by transfer of the magnetic particles from the nucleic acid extraction liquid into the nucleic acid amplification reaction liquid.

(7) The method according to the above (6), wherein the magnetic particles and the extracted nucleic acid are cleaned in a droplet which is composed of a cleaning liquid and is present in the container in a position different from positions in which the droplet composed of the nucleic acid amplification reaction liquid and the droplet composed of the nucleic acid extraction liquid are present, and then are transported by transfer of the magnetic particles from the droplet composed of the cleaning liquid into the nucleic acid amplification reaction liquid.

(8) The method according to the above (6) or (7), wherein the magnetic particles and the extracted nucleic acid are exposed to a droplet which is composed of a nucleic acid releasing liquid and is present in the container in a position different from positions in which the droplet composed of the nucleic acid amplification reaction liquid and the droplet composed of the nucleic acid extraction liquid are present, and then are transported by transfer of the magnetic particles from the droplet composed of the nucleic acid releasing liquid into the nucleic acid amplification reaction liquid.

Effect of the Invention

According to the present invention, it is possible to provide a real-time nucleic acid amplification method capable of accurately detecting fluorescence based on an amplified product obtained by a nucleic acid amplification method performed in a droplet in a perfect closed system. Therefore, the present invention makes it possible to quickly and accurately perform analysis in genetic testing (especially in pathogen inspection or SNPs testing) for clinical diagnosis.

Figure 1:
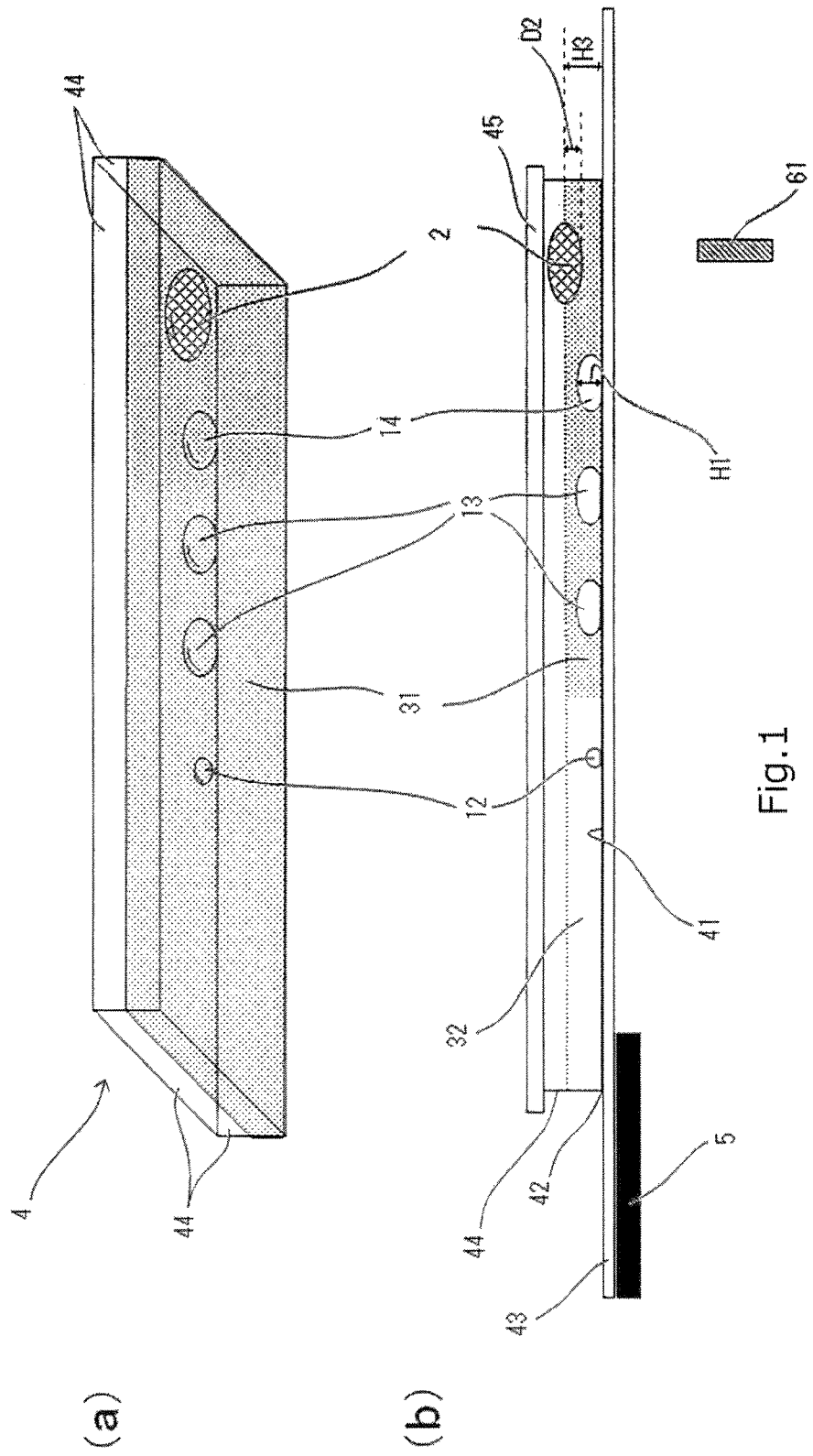
FIG. 1(a) is a perspective view of a container having a droplet encapsulating medium 31 filled therein, in which droplets (each of which is composed of a nucleic acid extraction liquid 14, a cleaning liquid 13, or a reaction liquid 12 for PCR) are encapsulated in the droplet encapsulating medium 31 and a droplet 2 composed of a nucleic acid-containing sample containing magnetic particles dispersed therein is placed on the droplet encapsulating medium 31.
FIG. 1(b) is a sectional view of the container shown in FIG. 1(a) provided with a cover 45, a substrate (ceramic plate) 43, and a heater 5 to create a temperature gradient.

DESCRIPTION OF REFERENCE NUMERALS 1 encapsulated droplet
3 droplet encapsulating medium
4 container
41 transport surface
5 heat source

MODES FOR CARRYING OUT THE INVENTION

1. Droplet

A droplet used in the present invention is a liquid lump having a shape (an almost spherical shape or its deformed shape) determined by a balance between a pressure difference between the inside and outside of a droplet comprising a liquid, and a surface tension generated by the intermolecular force of the liquid forming the droplet.

A liquid forming the droplet used in the present invention is not particularly limited as long as it is a water-based liquid insoluble or poorly soluble in a droplet encapsulating medium that will be described later, and may be water, an aqueous solution, or an aqueous suspension. The water-based liquid may contain any component to be subjected to a nucleic acid amplification reaction or an associated treatment performed for the nucleic acid amplification reaction to which the present invention can be applied. The associated treatment performed for the nucleic acid, amplification reaction include pretreatment, fractionation (separation), dissolution, mixing, dilution, stirring, and temperature control (heating and cooling), or the like.

In the present invention, specific examples of the liquid forming the droplet include a nucleic acid amplification reaction liquid for performing nucleic acid amplification reaction, a sample containing nucleic acid to be amplified, a nucleic acid extraction liquid for extracting nucleic acid, a magnetic particle cleaning liquid for cleaning nucleic acid, and a nucleic acid releasing liquid for releasing nucleic acid.

[1-1. Nucleic Acid Amplification Reaction Liquid]

The nucleic acid amplification reaction liquid used in the present invention contains to various elements usually used in a nucleic acid amplification reaction. In the present invention, said nucleic acid amplification reaction liquid contains at least nucleic acid to be amplified and magnetic particles.

[1-1-1. Various Elements Used in Nucleic Acid Amplification Reaction]

As will be described later, the nucleic acid amplification reaction is not particularly limited, and therefore the various elements used in a nucleic acid amplification reaction can be appropriately determined by those skilled in the art based on, for example, a known nucleic acid amplification method, examples of which will be mentioned later. Usually, a salt such as $MgCl_2$ or KCl, a primer, deoxyribonucleotides, a nucleic acid synthase, and a pH buffer solution are included. The above-mentioned salt to be used may be appropriately changed to another salt. There is a case where a substance for reducing non-specific priming, such as dimethylsulfoxide, is further added.

[1-1-2. Nucleic Acid to be Amplified]

A source of the nucleic acid to be amplified is not particularly limited. The nucleic acid to be amplified may be prepared by appropriately performing pretreatment on a separately-prepared sample containing nucleic acid. Examples of the pretreatment include treatments that are unaffected by a fluorochrome contained in the encapsulating medium, such as a treatment for extracting nucleic acid from a nucleic acid-containing sample, a treatment for cleaning magnetic particles to which nucleic acid is adsorbed, and a treatment for releasing nucleic acid from magnetic particles.

The sample containing nucleic acid to be amplified is not particularly limited, and examples thereof include living body-derived samples such as animal and plant tissues, bodily fluids, and excretions; and nucleic acid-containing materials such as cells, protozoa, fungi, bacterium, and viruses. The bodily fluids include blood, spinal fluid, saliva, and milk, and the excretions include feces, urine, and sweat, and they may be used in combination. The cells include white blood cells and platelets contained in blood; and exfoliated mucosal cells such as exfoliated oral mucosal cells and other exfoliated mucosal cells, and they may be used in combination. The nucleic acid-containing sample may be prepared as, for example, a mixture with a cell suspension, a homogenate, or a cell lysate.

It is to be noted that, in the present invention, an example of the nucleic acid-containing sample or a sample obtained by performing pretreatment on the nucleic acid-containing sample is sometimes referred to as a nucleic acid-containing liquid.

[1-1-3. Magnetic Particles]

In the present invention, magnetic particles are included in the droplet so that the droplet can be transferred by moving a magnetic field. The magnetic particles usually have hydrophilic groups on their surfaces.

The magnetic particles are not particularly limited as long as they are particles that respond to magnetism. Examples of such magnetic particles include particles having a magnetic substance such as magnetite, $\gamma$-iron oxide, manganese zinc ferrite, and the like. The magnetic particles may have surfaces having a chemical structure that specifically binds to a nucleic acid, such as an amino group, a carboxyl group, an epoxy group, avidin, biotin, digoxigenin, protein A, protein G, a complexed metal ion, or an antibody; or surfaces adapted to specifically bind to a polymer material by electrostatic force or Van der Waals force. This makes it possible to selectively adsorb the nucleic acid component to the surfaces of the magnetic particles.

Examples of the hydrophilic group on the surfaces of the magnetic particles include a hydroxyl group, an amino group, a carboxyl group, a phosphoric group, a sulfonic group, and the like.

The magnetic particles may further comprise, in addition to the above-mentioned elements, various elements appropriately selected by those skilled in the art. Specific preferred examples of the magnetic particles having hydrophilic groups on their surfaces include particles composed of a mixture of a magnetic substance and silica and/or an anion-exchange resin, magnetic particles whose surfaces are covered with silica and/or an anion-exchange resin, magnetic particles whose surfaces are covered with gold to which hydrophilic groups are attached via mercapto groups, and gold particles containing a magnetic substance and having surfaces to which hydrophilic groups are attached via mercapto groups.

The average particle diameter of the magnetic particles whose surfaces have hydrophilic groups may be about 0.1 μm to 500 μm. When the average particle diameter is small, the magnetic particles are likely to be present in a state where the particles are dispersed in the droplet.

As an example of commercially-available magnetic particles, Magnetic Beads provided as a constituent reagent of Plasmid DNA Purification Kit MagExtractor—Piasmid—sold by TOYOBO Co., Ltd. can be mentioned. When magnetic particles such as those sold as a constituent reagent of a kit are used, the magnetic particles are preferably cleaned by re-suspending an undiluted commercial liquid product, the liquid product dispersing magnetic particles, in pure water (e.g., in pure water whose amount is about ten times greater than that of the undiluted commercial liquid product). After being suspended in pure water, the magnetic particles can be cleaned by removing supernatant by a centrifugal operation. The suspending of the magnetic particles in pure water and removal of supernatant may be repeatedly performed. The cleaned magnetic particles may be used in the present invention in a dispersed state in pure water.

Such magnetic particles are incorporated into the droplet and therefore can be transferred together with the droplet in a direction, in which a means for applying a magnetic field is moved, by fluctuating a magnetic field. This makes it possible to transferred the droplet while the droplet keeps droplet state thereof.

[1-1-4. Blocking Agent]

The nucleic acid amplification reaction liquid used in the present invention may further contain, in addition to the above-mentioned components, a blocking agent. The blocking agent may be used to prevent deactivation of a nucleic acid polymerase due to adsorption to, for example, the inner wall of a reaction container or the surfaces of the magnetic particles.

Specific examples of the blocking agent include proteins such as bovine serum albumin (namely, BSA), other albumins, gelatin (namely, denatured collagen), casein, and polylysine; and peptides (all of which may be either natural or synthetic).

The nucleic acid amplification reaction to which the present invention is applied is not particularly limited, and examples of a method used to perform the nucleic acid amplification reaction include a PCR method (U.S. Pat. Nos. 4,683,195, 4,683,202, 4,800,159, and 4,965,188), a LCR method (U.S. Pat. No. 5,494,810), a Qβ method (U.S. Pat. No. 4,786,600), a NASBA method (U.S. Pat. No. 5,409,818), a LAMP method (U.S. Pat. No. 3,313,358), an SDA method (U.S. Pat. No. 5,455,166), an RCA method (U.S. Pat. No. 5,354,688), an ICAN method (Japanese Patent No. 3433929), and a TAS method (Japanese Patent No. 2843586).

The composition of the reaction liquid required for the nucleic acid amplification reaction and the reaction temperature can be appropriately selected by those skilled in the art.

In a real-time nucleic acid amplification method, an amplified product is labeled with a fluorochrome that can stain double-stranded DNA, and therefore a change in the fluorochrome can be observed by heating the double-stranded DNA.

Examples of a detecting method used in such a real-time nucleic acid amplification method include the following methods.

For example, when only a desired target can be amplified by a highly specific primer, an intercalator method using, for example, SYBR (Registered trade mark) GREEN I is used.

An intercalator that emits fluorescence when binding to double-stranded DNA binds to double-stranded DNA synthesized by a nucleic acid amplification reaction, and emits fluorescence by irradiation with exciting light. By detecting the intensity of the fluorescence, the amount of amplified product produced can be monitored. This method is not required to design and synthesize a fluorescence-labeled probe specific to a target, and is therefore easily used to measure various targets.

When it is necessary to distinctively detect very similar sequences or SNPs typing is performed, a probe method is used. An example of the probe method is a TaqMan (Registered trade mark) probe method using, as a probe, an oligonucleotide whose 5' end is modified with a fluorescent material and 3' end is modified with a quencher material.

The TaqMan probe is specifically hybridized with template DNA in an annealing step, but even when the fluorescent material is irradiated with exciting light, fluorescence emission is suppressed by the quencher present in the probe. In an extension reaction step, the TaqMan probe hybridized with the template is decomposed by the 5'→3' exonuclease activity of TaqDNA polymerase so that the fluorochrome is released from the probe, and therefore suppression by the quencher is cancelled and fluorescence is emitted. By measuring the intensity of the fluorescence, the amount of amplified product produced can be monitored.

The principles on which DNA is quantified by real-time PCR by such a method will be described below. First, PCR is performed using, as templates, standard samples of known concentrations prepared by serial dilution to determine threshold cycles (Ct values) at which the amount of amplified product reaches a certain level. The Ct values are plotted along a lateral axis and the initial amounts of DNA are plotted along a vertical axis to prepare a calibration curve.

A PCR reaction is performed also on a sample of an unknown concentration under the same conditions to determine a Ct value. The amount of target DNA contained in the sample can be determined from the Ct value and the above-mentioned calibration curve.

The melting curve of the amplified product can also be obtained by further irradiating the amplified product with exciting light from thermal denaturation to annealing.

Double-stranded DNA generated by a nucleic acid amplification reaction has an inherent Tm value depending on DNA length and base sequence. That is, when the temperature of a droplet containing DNA labeled with a fluorochrome is gradually increased, a temperature at which fluorescence intensity rapidly decreases is detected. As a result of examination of the amount of change in fluorescence intensity, a temperature peak thereof is in close agreement with a Tm value defined by the base sequence and length of the DNA. This makes it possible to exclude data observed by generation of not a target gene but, for example, a primer dimer (i.e., false-positive data) from positive data. In genetic testing, a non-specific reaction often occurs due to foreign substances contained in a sample, and therefore exclusion of such false-positive data is important. Further, it is also possible to determine whether or not the amplified product is specific to a target gene,

[1-2. Nucleic Acid Extraction Liquid]

As the nucleic acid extraction liquid used to extract nucleic acid, a buffer solution containing a chaotropic material, EDTA, Tris-HCl, etc. can be mentioned. Examples of the chaotropic material include guanidinium hydrochloride, guanidine isothiocyanate, potassium iodide, urea, and the like.

A specific method for extracting nucleic acid from a nucleic acid-containing sample can be appropriately determined by those skilled in the art. In the present invention, magnetic particles are used to transport nucleic acid in the droplet encapsulating medium, and therefore a nucleic acid extraction method using magnetic particles is preferably used. For example, nucleic acid can be extracted from a nucleic acid-containing sample and purified using magnetic particles with reference to JP-A-2289596.

[1-3. Cleaning Liquid]

As the cleaning liquid, any cleaning liquid can be used as long as it is a solution that can dissolve components (e.g., proteins and sugars) other than nucleic acid contained in a nucleic acid-containing sample, or components of a reagent or the like used in previously-performed another treatment such as nucleic acid extraction, while allowing nucleic acid to remain adsorbed to the surfaces of magnetic particles. Specific examples of such a cleaning liquid include high-salt concentration aqueous solutions such as sodium chloride, potassium chloride, ammonium sulfate, and the like; and alcohol aqueous solutions such as ethanol, isopropanol, and the like.

A specific method for cleaning the magnetic particles to which nucleic acid is adsorbed can also be appropriately determined by those skilled in the art. The frequency of cleaning of the magnetic particles to which nucleic acid is adsorbed can be appropriately determined by those skilled in the art so that a nucleic acid amplification reaction is not undesirably inhibited. From the same viewpoint, the cleaning step may be omitted.

The number of droplets composed of the cleaning liquid may be at least the same as the frequency of cleaning.

[1-4. Nucleic Acid Releasing Liquid]

As the nucleic acid releasing liquid, water or a buffer solution containing a low concentration of salt can be used. Specific examples of such a nucleic acid releasing liquid include Tris buffer solutions, phosphate buffer solutions, and distilled water.

A specific method for releasing nucleic acid from magnetic particles to which the nucleic acid is adsorbed can also be appropriately determined by those skilled in the art.

[1-5. Amount of Droplet]

The amount of the droplet completely encapsulated in the encapsulating medium may be, for example, 0.1 µL to 10 µL, or 0.01 µL to 1,000 µL.

2. Droplet Encapsulating Medium

As the droplet encapsulating medium, a chemically-inactive material insoluble or poorly soluble in the liquid constituting the droplet is used. The chemically-inactive material refers to a material having no chemical influence on the liquid constituting the droplet during various operations such as droplet fractionation (separation), mixing, dissolution, dilution, stirring, heating, and cooling. In the present invention, a water-insoluble or poorly water-soluble material is usually used as the droplet encapsulating medium.

Examples of such a material include: hydrocarbons such as alkanes; perfluoroalkanes; fluorinated alkanes in which at least part of hydrogen atoms in alkanes is substituted with fluorine; mineral oils; silicone oils; fatty acids; fatty acid esters; fatty acid amides; fatty acid ketones; fatty acid amines; and water-insoluble or poorly water-soluble liquid materials. Among these materials, materials having a specific gravity less than 1 are preferably used. When a material having a specific gravity less than 1 is used, the droplet sinks in the droplet encapsulating medium and therefore can be easily manipulated by fluctuating a magnetic field.

Further, there is a case where a heat-resistant enzyme is used in a nucleic acid amplification reaction, and therefore when the heat-resistant enzyme has a relatively high optimum temperature, a low-volatile material is preferably used as the droplet encapsulating medium. More specifically, a material having a boiling point of 200° C. or lower is preferably used. Preferred specific examples of such a material to be used include mineral oils, silicone oils (usually, dimethyl silicone), fatty acid esters, fats and oils, and the like.

Alternatively, a material that can dissolve a fluorescent material to be used may be appropriately selected by those skilled in the art. For example, a material having a phenyl group or the like as a component having a certain level of intramolecular polarity is sometimes preferred. More specifically, a phenyl group-containing silicone oil such as diphenyldimethicone can be used as a material for the droplet encapsulating medium.

In the present invention, as the droplet encapsulating medium, a material that can fix the droplet when treatments (nucleic acid amplification reaction and other treatments) are not performed in the droplet can be used. The use of such a material is preferred in that a container in which the droplet is encapsulated in the droplet encapsulating medium can be easily and safely handled during storage or transport. Such an embodiment can be achieved by using, as the droplet encapsulating medium, a material that has flowability allowing droplet transfer when treatment is performed in the droplet but does not have such flowability when treatment is not performed in the droplet.

[2-1. Droplet Encapsulating Medium with Melting Point Lower than Reaction Temperature]

As the droplet encapsulating medium, one having a melting point lower than a temperature at which a nucleic acid amplification reaction occurs can be used. In this case, before the start of a nucleic acid amplification reaction, the droplet encapsulating medium is put into a state not having flowability (i.e., a solid state) allowing the droplet transfer. This makes it possible to fix the droplet at an arbitrary position to prevent the droplet from moving in an unexpected direction. On the other hand, in order to start a nucleic acid amplification reaction, the droplet is able to be transferred by, for example, heating the droplet encapsulating medium to put the medium into a state having flowability (i.e., a melt state).

For example, a material having a melting point of ordinary temperature (20° C.±15° C.) can be used as the droplet encapsulating medium. This makes it possible to solidify the droplet encapsulating medium at a cold storage temperature generally used and therefore to easily store a reaction container or a reaction substrate. Examples of such a material include straight chain alkanes having about 16 to 23 carbon atoms. A specific example of such an alkane is octadecane that is an alkane having 17 carbon atoms (a straight chain alkane having a melting point of about 28 to 30° C.).

The flowability allowing droplet displacement can be achieved by using, as the droplet encapsulating medium, a material having a kinetic viscosity of 5 mm$^2$/s to 100 mm$^2$/s (at 25° C.) at a temperature equal to or lower than a melting point of the medium. Particularly, when a nucleic acid amplification reaction that requires a high temperature condition near 100° C. is performed, a material having such a kinetic viscosity is preferably used. If the kinetic viscosity is less than 5 mm$^2$/s, the droplet encapsulating medium is likely to volatilize at a high temperature. On the other hand, if the kinetic viscosity exceeds 100 mm$^2$/s, transfer of the droplet achieved by fluctuating a magnetic field is likely to be inhibited. As one example of such a material preferably used as the droplet encapsulating medium, a silicone oil can be mentioned.

[2-1. Droplet Encapsulating Medium with Gel-Sol Transition Point Lower than Reaction Temperature]

As the droplet encapsulating medium, a material having a gel-sol transition point lower than a temperature of nucleic acid amplification reaction. The droplet encapsulating medium used in this case is in a gel state at least before droplet manipulation; and is insoluble or poorly soluble in the nucleic acid amplification reaction liquid constituting the droplet in both cases where the medium is in the gel state, and where a temperature of the medium exceeds a gel-sol transition point thereof and the medium is turned into a sol state. In the present invention, a water-insoluble or poorly water-soluble liquid material that can be turned into a gel by adding a gelling agent is usually used.

[2-2-1. Gel-Sol Transition Point]

When the droplet encapsulating medium is exposed to a temperature lower than the gel-sol transition point thereof, the droplet encapsulating medium is turned into a state not having flowability (i.e., a gel state) allowing the transfer of the droplet encapsulated in the droplet encapsulating medium. This makes it possible to fix the droplet at an arbitrary position to prevent the droplet encapsulated in the droplet encapsulating medium from moving in an unexpected direction. Further, it is also possible, while the droplet encapsulated in the droplet encapsulating medium is fixed in such a manner as described above, to easily transfer the magnetic particles contained in the droplet and a material adsorbed to the magnetic particles (more specifically, a nucleic acid or a liquid that is adsorbed to the surfaces of the magnetic particles, and is to be subjected to a reaction or a treatment). Therefore, even when encapsulated droplets are arranged in positions close to each other, they are not mixed together and therefore magnetic particles and a material adsorbed thereto can be easily moved between these encapsulated droplets.

On the other hand, in order to start a nucleic acid amplification reaction, the droplet encapsulating medium is exposed to a temperature higher than the gel-sol transition point thereof by heating, and is turned into a state having flowability (i.e., a sol state). This makes it possible to transfer said encapsulated droplet. Even when the volume of the droplet is relatively larger than the total volume of the magnetic particles, the entire droplet can be transferred.

By placing such a droplet encapsulating medium in a temperature variable region that will be described later, as shown in FIG. 1(b), it is possible to easily achieve a state where both a phase of a gel 31 having no flowability and a phase of a sol 32 having flowability coexist in the same container.

The sol-gel transition point can be set to 40 to 60° C.

The sol-gel transition point may vary depending on conditions such as the type of oil used, the type of gelling agent used, and the amount of gelling agent added. Therefore, such conditions are appropriately selected by those skilled in the art so that a desired sol-gel transition point can be achieved.

[2-2-2. Water-Insoluble or Poorly Water Soluble Liquid Material]

In an embodiment in which a droplet encapsulating medium having a gel-sol transition point lower than a temperature of nucleic acid amplification reaction, a material obtained by adding a gelling agent into a water-insoluble or poorly water-soluble liquid material is used as the droplet encapsulating medium. As the water-insoluble or poorly water-soluble liquid material used in this embodiment, an oil whose solubility in water at 25° C. is about 100 ppm or less and which is in a liquid state at an ordinary temperature (20° C.±15° C.) may be used. For example, such an oil may be one or a combination of two or more selected from the group consisting of liquid fats and fatty oils, an ester oil, a hydrocarbon oil, and a silicone oil.

Examples of the liquid fats and fatty oils include linseed oil, camellia oil, macadamia nut oil, corn oil, mink oil, olive oil, avocado oil, sasanqua oil, castor oil, safflower oil, persic oil, cinnamon oil, jojoba oil, grape seed oil, sunflower oil, almond oil, rape oil, sesame oil, wheat germ oil, rice germ oil, rice bran oil, cottonseed oil, soybean oil, peanut oil, tea oil, evening primrose oil, egg-yolk oil, liver oil, coconut oil, palm oil, palm kernel oil, and the like.

Examples of the ester oil include: octanoic acid esters such as cetyl octanoate; lauric acid esters such as hexyl laurate; myristic acid esters such as isopropyl myristate and octyldodecyl myristate; palmitic acid esters such as octyl palmitate; stearic acid esters such as isocetyl stearate; isostearic acid esters such as isopropyl isostearate; isopalmitic acid esters such as octyl isopalmitate; oleic acid esters such as isodecyl oleate; adipic acid esters such as isopropyl adipate; sebacic acid esters such as ethyl sebacate; malic acid esters such as isostearyl malate; glyceryl trioctanoate; glyceryl triisopalmitate, and the like.

Examples of the hydrocarbon oil include pentadecane, hexadecane, octadecane, mineral oil, liquid paraffin, and the like.

Examples of the silicone oil include dimethyl polysiloxane; phenyl group-containing silicone oils such as methyl phenyl polysiloxane and others; methylhydrogen polysiloxane, and the like.

[2-2-3. Gelling Agent]

As the gelling agent, one oil gelling agent or a combination of two or more oil gelling agents selected from the group consisting of hydroxy fatty acids, dextrin fatty acid esters, and glycerin fatty acid esters may be used.

The hydroxy fatty acids are not particularly limited as long as they are fatty acids having a hydroxyl group. Specific examples of such hydroxy fatty acids include hydroxymyristic acid, hydroxypalmitic acid, dihydroxypalmitic acid, hydroxystearic acid, dihydroxystearic acid, hydroxymargaric acid, ricinoleic acid, ricinelaidic acid, linolenic acid, and the like. Among them, hydroxystearic acid, dihydroxystearic acid, and ricinoleic acid are preferred. These hydroxy fatty acids may be used singly or in combination of two or more of them. An animal and plant oil fatty acid (e.g., castor oil fatty acid, hydrogenated castor oil fatty acid, or the like) which is a mixture of two or more of the above-mentioned examples may also be used as the hydroxy fatty acid.

Examples of the dextrin fatty acid esters include dextrin myristate (manufactured by Chiba Flour Milling Co., Ltd. under the trade name of "Rheopearl MKL"), dextrin palmitate (manufactured by Chiba Flour Milling Co., Ltd. under the trade name of "Rheopearl KL" or "Rheopearl TL"), and dextrin palmitate/2-ethylhexanoate (manufactured by Chiba Flour Milling Co., Ltd. under the trade name of "Rheopearl TT").

Examples of the glycerin fatty acid esters include glyceryl behenate, glyceryl octastearate, and glyceryl eicosanoate. These glycerin fatty acid esters may be used singly or in combination of two or more of them. Specific examples of the glycerin fatty acid ester include "TAISET 26 (trade name)" (manufactured by Taiyo Kagaku Co., Ltd.) containing 20% glyceryl behenate, 20% glyceryl octastearate, and 60% hardened palm oil, and "TAISET 50 (trade name)" (manufactured by Taiyo Kagaku Co., Ltd.) containing 50% glyceryl behenate and 50% glyceryl octastearate.

The amount of the gelling agent to be added to the water-insoluble or poorly water-soluble liquid material is, for example, 0.1 to 0.5 wt %, 0.5 to 2 wt %, or 1 to 5 wt % of the total weight of the liquid material. However, the amount of the gelling agent to be added is not particularly limited thereto, and can be appropriately determined by those skilled in the art so that a desired gel-sol state can be achieved.

A gelation method can be appropriately determined by those skilled in the art. More specifically, the water-insoluble or poorly water-soluble liquid material is heated, the gelling agent is added to and completely dissolved in the heated liquid material to obtain a solution, and then the solution is cooled. The heating temperature may be appropriately determined in consideration of the physical properties of the liquid material used and the physical properties of the gelling agent used. For example, the heating temperature is sometimes preferably about 60 to 70° C. The dissolution of the gelling agent is preferably performed by gently mixing the liquid material and the gelling agent. The cooling is preferably slowly performed. For example, the cooling may be performed in about 1 to 2 hours. The cooling can be completed by lowering the temperature of the solution to, for example, an ordinary temperature (20° C.±15° C.) or lower, preferably 4° C. or lower. As the above-mentioned preferred example of the gelation method, one using the above-mentioned "TAISET 26" (manufactured by Taiyo Kagaku Co., Ltd.) can be mentioned.

[2-2-4. Example of Droplet Encapsulating Medium]

An example of the desired gel-sol state is one in which the above-mentioned sol-gel transition point can be achieved.

Another example of the desired gel-sol state is one in which a gel state where a completely-encapsulated droplet can be properly fixed can be achieved. A preferred example of the state where the completely-encapsulated droplet is properly fixed is one in which the encapsulated droplet is not moved by an external force on the order of at least gravity. The phrase "not moved" preferably means that a position where a droplet is in contact with the bottom surface of a container is hardly changed.

Figure 2:
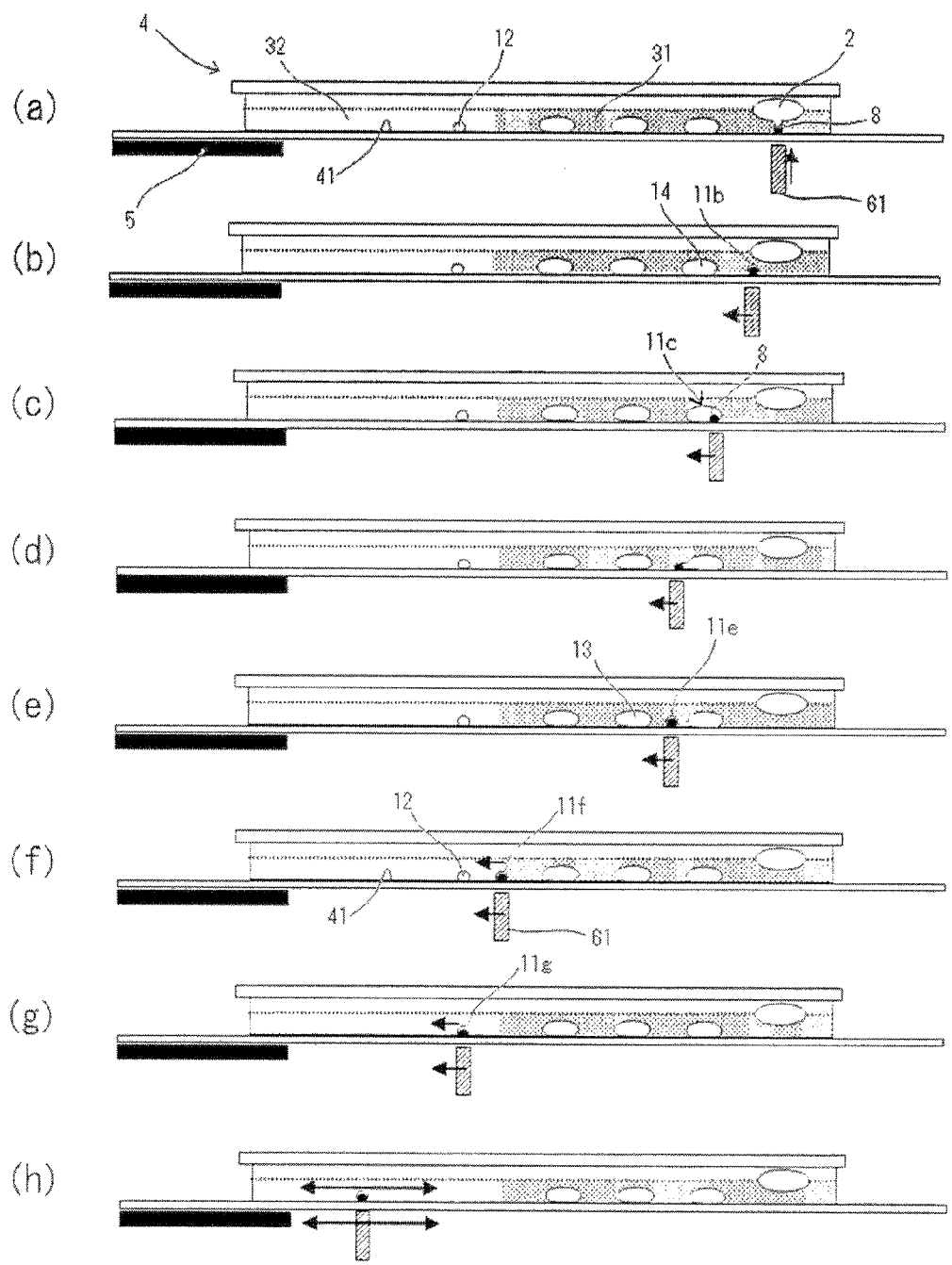
FIGS. 2(a) to 2(h) are schematic views of the container shown in FIG. 1 in which a nucleic acid amplification reaction is performed by sampling the nucleic acid-containing sample from the droplet 2 together with the magnetic particles 3 dispersed in the droplet 2 by manipulation using a magnet 61 (FIG. 2(a)); transferring the sampled nucleic acid-containing sample together with the magnetic particles 8 (FIG. 2(b)); extracting nucleic acid (FIG. 2(c)); transferring a sample containing the extracted nucleic acid together with the magnetic particles (FIG. 2(d)); cleaning the sample and the magnetic particles, and coalescing the nucleic acid and the magnetic particles with the nucleic acid amplification reaction liquid 12 (FIGS. 2(e) and 2(f)); and transferring the reaction liquid to a spot having a temperature necessary for nucleic acid amplification (FIG. 2(g)).

Another example of the desired gel-sol state is one in which when, as shown in FIG. 1(b), a droplet 2 of about 0.05 to 5 μL (provided as an aqueous solution or a suspension) containing about 10 to 1000 μg of magnetic particles is placed on a gel-state droplet encapsulating medium 31, and then, as shown in FIG. 2(a), a magnetic field is applied by a magnet 61 from the bottom surface side of a container, magnetic particles 8 contained in the droplet 2 respond to the magnetic field and sink to the bottom surface of the container together with a material adsorbed to the magnetic particles 8.

Another example of the desired gel-sol state is one in which the droplet encapsulating medium in a sol state has a kinetic viscosity of 5 $mm^2/s$ to 100 $mm^2/s$, preferably 5 $mm^2/s$ to 50 $mm^2/s$, for example, about 20 $mm^2/s$ (25° C.). Particularly, when a nucleic acid amplification reaction that requires a high temperature condition near 100° C. is performed, the droplet encapsulating medium to be used preferably has such a kinetic viscosity. If the kinetic viscosity is less than 5 $mm^2/s$, the droplet encapsulating medium is likely to volatilize at a high temperature, and on the other hand, if the kinetic viscosity exceeds 100 $mm^2/s$, transfer of the droplet achieved by fluctuating a magnetic field is likely to be inhibited. As one of materials preferably used as such a droplet encapsulating medium, one obtained by adding a gelling agent to a silicone oil can be mentioned.

As for the physical properties of the droplet encapsulating medium in a gel state, its storage viscoelasticity E', which is one of dynamic viscoelastic properties, is preferably 10 to 100 kPa, more preferably 20 to 50 kPa at an ordinary temperature (20° C.±15° C.).

[2-3. Amount of Encapsulating Medium]

The amount of the droplet encapsulating medium used can be determined without any limitation as long as it is enough to completely encapsulate the droplet. The present invention allows the droplet encapsulating medium to be used in such an amount that makes it impossible to adequately detect an amplified product in the case of a conventional method (i.e., a method in which a fluorescent material is added only to a droplet at the start of a nucleic acid amplification reaction).

More specifically, the droplet encapsulating medium can be used in an amount 1,000 to 100,000 times or 3,000 to 10,000 times the volume of the droplet. The use of the droplet encapsulating medium in an amount within the above range is preferred in that the droplet can be transported with high manipulability. If the amount of the droplet encapsulating medium used exceeds the above upper limit, it tends to take a long time to create temperature conditions suitable for the start of PCR to start analysis. On the other hand, if the amount of the droplet encapsulating medium used is less than the above lower limit, the amount of the fluorochrome contained in the droplet is excessive and therefore an S/N ratio tends to lower due to background rise during fluorescence detection. On the other hand, if the amount of the droplet encapsulating medium used exceeds the above upper limit, detection sensitivity tends to lower due to diffusion of the fluorochrome from the droplet.

The droplet encapsulating medium is contained in a container. More specifically, as shown in FIG. 1(b), the droplet encapsulating medium is filled in a container so as to come into contact with a transport surface 41. In this case, the filling height (filling thickness) H3 of the droplet encapsulating medium in the container can be determined without any limitation as long as the amount of the droplet encapsulating medium is enough to completely encapsulate the droplet. Usually, the filling height H3 can be made equal to or larger than a height H1 of the droplet encapsulated in the droplet encapsulating medium.

Figure 5:
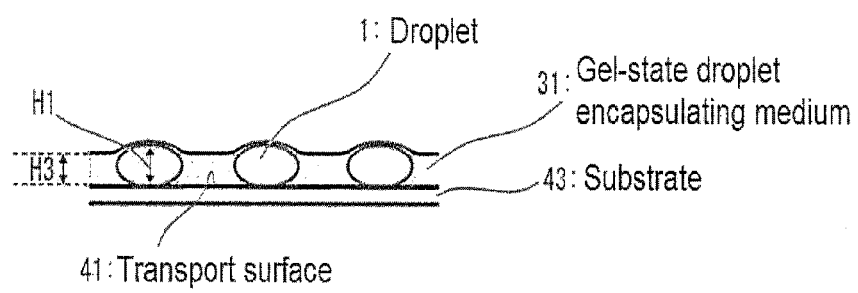
FIGS. 5(a) and 5(b) show other examples of droplet encapsulation.
Figure 5:
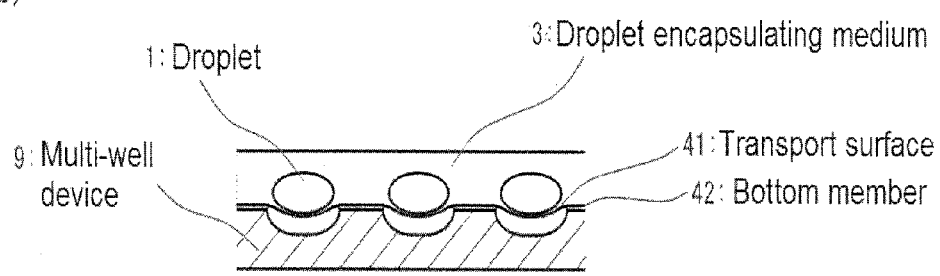

The droplet encapsulating medium used in the present invention has an excellent ability to encapsulate the droplet, and therefore the following embodiment is acceptable. That is, as shown in FIG. 5(a), an embodiment in which a filling height H3 of part of the droplet encapsulating medium where droplets 1 are not present in a container is lower than the height H1 of the encapsulated droplet (which has the largest volume among the encapsulated droplets in the container) is also acceptable.

3. Fluorescent Material

The fluorescent material is included in at least the droplet encapsulating medium. The fluorescent material needs to be contained in at least the droplet encapsulating medium at the start of the nucleic acid amplification reaction at the latest. It is to be noted that it has already been confirmed by the present inventors that when pretreatment for the nucleic acid amplification reaction is also performed in another droplet in the same droplet encapsulating medium, the fluorescent material does not affect the pretreatment even when the fluorescent material is contained in the droplet encapsulating medium in the stage of the pretreatment.

The fluorescent material is not particularly limited, and one used to detect nucleic acid in a nucleic acid amplification reaction can be appropriately determined by those skilled in the art. Specific examples of such a fluorescent material include SYBR® GREEN I, ethidium bromide, SYTO®-13, SYTO®-16, SYTO®-60, SYTO®-62, SYTO®-64, SYTO®-82, POPO®-3, TOTO®-3, BOBO®-3, TO-PRO®-3, YO-PRO®-1, SYTOX Orange®, and the like.

If a fluorochrome molecule is contained only in the droplet at the start of a nucleic acid amplification reaction, the fluorochrome molecule diffuses from the droplet into the droplet encapsulating medium, which makes it difficult to detect an amplified product. Therefore, according to the present invention, the fluorochrome molecule is contained in the droplet encapsulating medium for the purpose of making up for the fluorochrome molecule expected to diffuse.

The fluorochrome molecule may be included only in the droplet encapsulating medium at the start of a nucleic acid amplification reaction. In this case, the fluorochrome molecules initially contained in the droplet encapsulating medium first penetrates the droplet, which makes it possible to detect nucleic acid.

Alternatively, the fluorochrome molecule may be contained in both the droplet and the droplet encapsulating medium at the start of nucleic acid synthesis. The specific concentration of the fluorescent molecule in the droplet and the specific concentration of the fluorescent molecule in the droplet encapsulating medium are not particularly limited. For example, the concentration of the fluorescent molecule in the droplet is sometimes preferably adjusted so as to be higher than that of the fluorescent molecule in the droplet encapsulating medium. This is because a pressure at which the fluorochrome contained in the droplet encapsulating medium penetrates the droplet is high, and therefore the concentration of the fluorochrome in the droplet can be made constant by setting the concentration of the fluorochrome in the droplet encapsulating medium low.

As described above, by allowing the fluorochrome molecule to be contained in at least the droplet encapsulating medium, it is possible to maintain the concentration of the fluorochrome in the droplet at such a level that an amplified product can be stably detected while a nucleic acid amplification reaction keeps going. The method according to the present invention makes it possible to properly maintain the concentration of the fluorochrome in the droplet and therefore to effectively detect an amplified product even at the end of a nucleic acid amplification reaction.

More specifically, the concentration of the fluorochrome contained in the droplet encapsulating medium can be set to 0.01 to 0.5 µM. The upper limit of the concentration may be set to 0.2 µM, 0.1 µM, 0.05 µM, or 0.02 µM. The lower limit of the concentration may be set to 0.02 µM, 0.05 µM, 0.1 µM, or 0.2 µM.

On the other hand, the concentration of the fluorochrome contained in the droplet can be set to 0 to 20 µM. The upper limit of the concentration may be set to 10 µM, 5 µM, 2 µM, 1 µM, or 0.5 µM. The lower limit of the concentration may be set to 0.5 µM, 1 µM, 2 µM, 5 µM or 10 µM. The concentration within the above range is preferred in that it is easy to stably detect an amplified product while a reaction keeps going.

According to the present invention, for example, there is a case where the concentration of the fluorochrome in the droplet encapsulating medium is preferably 0.05 to 0.1 µM, and the concentration of the fluorochrome in the droplet is preferably 0.5 µM to 2 µM.

4. Container

The container is not particularly limited as long as the container can hold the droplet encapsulating medium, and an inner wall of the container has a transport surface on which the droplet is transferred (i.e., with which the droplet is in direct contact). The shape of the container is not particularly limited. For example, the container may comprise a substrate 43 having a transport surface 41 shown in FIG. 5(a); or the container may comprise a bottom member 42 having a transport surface 41 and provided on and in contact with a substrate (ceramic plate) 43, and a wall 44 surrounding the transport surface 41 shown in FIG. 1(b).

As shown in FIG. 1(b), the container may further comprise a cover 45 with which a space surrounded by the wall 44 is covered to close the space. The cover 45 may be configured to be fully or partially openable and closable so that a reagent for performing a treatment such as a nucleic acid amplification reaction or a droplet containing a sample can be charged into the container.

From the viewpoint of constructing a perfect closed system, the reaction container is preferably formed by integrally molding a substrate or a bottom member having a transport surface or a wall; or by integrally molding a substrate or a bottom member having a transport surface, a wall, and a cover. Constructing a perfect closed system is very effective because it is possible to prevent contamination with foreign matters during treatment,

[4-1. Material]

The material of the substrate or the bottom member having a transport surface is not particularly limited, but the transport surface is preferably water repellent to reduce resistance to transfer of the droplet. Examples of a material that imparts such a property include resin materials such as polypropylene, Teflon (Registered Trade Mark), polyethylene, polyvinyl chloride, polystyrene, polycarbonate, and the like. On the other hand, when, the container used has a bottom member having a transport surface and provided on a substrate, the substrate may be made of any one of the above-mentioned materials or another material such as ceramic, glass, silicone, or metal.

According to the present invention, the material of the substrate or the bottom member is preferably a resin, particularly preferably polypropylene. When the bottom member is used, a film is preferably used as the bottom member. More specifically, an extra-thin film having a thickness of, for example, 3 µm or less may be used. From the viewpoint of heat resistance required during a nucleic acid amplification reaction, water repellency required during droplet transfer, adhesiveness, processability, and low cost, an extra-thin polypropylene film is preferably used as the bottom member.

Part of the transport surface that is in contact with the droplet and the droplet encapsulating medium may have an affinity for the droplet. For example, such part of the transport surface may be previously subjected to a treatment for relatively reducing water repellency, or a treatment for relatively enhancing hydrophilicity, or a treatment for relatively increasing surface roughness. By placing the droplet in such part of the transport surface, it is possible, even when the droplet encapsulating medium has flowability, to prevent the encapsulated droplet from unintentionally moving.

[4-2. Physical Properties]

The substrate and the bottom member preferably have light permeability. This makes it possible to perform optical detection when the absorbance of the droplet, fluorescence, chemiluminescence, bioluminescence, or refractive index change is measured from the outside of the reaction container or from the back surface side of the reaction substrate.

Further, the substrate and the bottom member preferably have a surface that can maintain a large contact angle with the droplet even at a high temperature at which a nucleic acid amplification reaction can be performed. More specifically, polypropylene, or a resin that has a contact angle with the droplet equal to or larger than that of polypropylene with the droplet is preferably used. The contact angle of the droplet on the surface of the substrate is preferably about 95° (deg) to 135° (deg) (at 25° C.).

The transport surface that is in contact with the droplet and the droplet encapsulating medium is preferably a smooth surface to transfer the droplet. Particularly, the transport surface preferably has a surface roughness Ra of 0.1 µm or less. For example, when the droplet is transferred by fluctuating a magnetic field by bringing a permanent magnet close to the substrate from the bottom side of the container, the magnetic particles are transferred while being pressed against the surface of the substrate. In this case, by allowing the transport surface to have a surface roughness Ra of 0.1 µm or less, it is possible for the magnetic particles to sufficiently follow the movement of the permanent magnet.

[4-3. Temperature Variable Region]

The transport surface on which the droplet is transferred has a temperature variable region. The temperature variable region is provided by creating a temperature gradient so that a temperature is continuously changed along a droplet transport path on the transport surface. The temperature gradient is created by, for example, bringing a heat source 5 into contact with part of the bottom surface of the container or part of a substrate 43 shown in FIG. 1(b) which is in contact with the bottom surface of the container, and then heating the heat source 5 at a constant temperature. This makes it possible to provide, on the surface of the substrate or on the surface of the bottom member, a temperature variable region having such a temperature gradient that a temperature is highest at a point located just above the heat source and decreases with the distance from the heat source.

The droplet can be transferred in the temperature variable region by fluctuating a magnetic field and placed at a point having a temperature required for a treatment to be performed. The temperature of the liquid constituting the droplet can be quickly adjusted to the temperature of the point simply by transferring the droplet. Therefore, as in the case of a nucleic acid amplification reaction, even when a reaction to be performed requires a temperature change, the temperature of the droplet can be quickly and easily increased and decreased by simply transferring the droplet.

The heat source is set to a temperature highest among temperatures required for a reaction to be performed or higher. Further, a cooling source such as a heat sink plate, a cooling fan, or the like may be provided on the low-temperature side of the temperature gradient whose high-temperature side is in contact with the heat source. By providing such a cooling source, it is possible to increase the temperature gradient created in the temperature variable region.

The temperature gradient created in the temperature variable region can be increased also by using a material having low heat conductivity, such as a resin, as a material for the substrate or the bottom member. This makes it possible to perform local temperature adjustment in a narrow region.

By increasing the temperature gradient in this way, it is possible, even when two or more temperature conditions having a relatively large temperature difference are required for a treatment to be performed, to shorten the moving distance of the droplet. This makes it possible to efficiently perform the treatment and reduce the size of the reaction container.

5. Magnetic-Field Applying Means

A magnetic-field applying means or a magnetic-field moving system for fluctuating a magnetic field to transfer the droplet is not particularly limited. As the magnetic-field applying means, a magnetism source such as a permanent magnet (e.g., a ferrite magnet or a neodymium magnet), an electromagnet, or the like can be used. The magnetism source can be provided outside the container in a state where the magnetic particles dispersed in the droplet present in the container can aggregate on the transport surface side. This makes it possible for the magnetism source to apply a magnetic field to the magnetic particles present via the transport surface of the container to capture the aggregated magnetic particles and the droplet containing the magnetic particles.

As the magnetic-field moving system, for example, a system can be used which can move a magnetic field along the transport surface in a state where the magnetic particles can remain aggregated.

Figure 4:
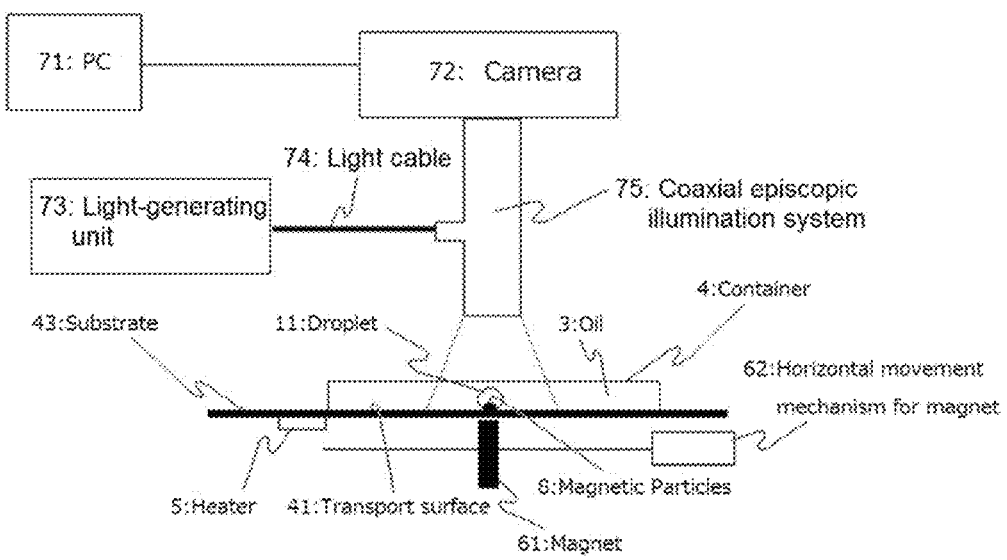
FIG. 4 is a schematic diagram showing the configuration of equipment for performing PCR by transferring a droplet 11, which is composed of a reaction liquid for PCR containing magnetic particles 8 and is encapsulated in a droplet encapsulating medium 3 filled in a container 4, with the use of a magnet 61 to detect a PCR product in real time during PCR by fluorescence detection.

For example, as shown in FIG. 4, a system 62 can be used which can mechanically move a magnetism source (e.g., a magnet 61) itself approximately parallel to a transport surface 41. Magnetic particles 8 and a droplet 11 containing the magnetic particles 8 captured via the bottom surface of the container by the magnetism source 61 follow the movement of the magnetism source and therefore can be transferred on the transport surface 41. This makes it possible to transfer the encapsulated droplet, separate a small droplet from the encapsulated droplet regarded as a main (mother) droplet, and coalesce the encapsulated droplet with another encapsulated droplet.

As the magnetic-field moving system, a system that can block or reduce a magnetic field applied to the magnetic particles is also preferably provided. In this case, the system is required to block or reduce a magnetic field to such a degree that the aggregated magnetic particles can be disaggregated and dispersed in the droplet.

For example, an electric current control means can be used. Alternatively, for example, a system can be used which can move a magnet, which is provided via the transport surface outside the container, in a direction approximately perpendicular to the transport surface. In this case, by moving the magnet away from the transport surface, it is possible to block or reduce a magnetic field. This makes it possible to disperse the magnetic particles in the encapsulated droplet to sufficiently expose a component adsorbed to the magnetic particles to the liquid constituting the encapsulated droplet.

Further, a means that can control fluctuations in magnetic field can also be provided. For example, a means which is equipped with a function of vibrating the magnetism source can be used in place of a stirrer. This makes it easy to mix the droplet with another droplet or perform stirring.

As another example of the system that can move a magnetic field along the transport surface, a system that does not involve the above-mentioned mechanical movement of the magnetism source itself may be used. Such a system can be achieved by an array of electromagnets one-dimensionally or two-dimensionally arranged approximately parallel to the transport surface and an electric current control means. In this case, the droplet can be captured by the passage of electric current through the electromagnets and the droplet can be transferred or the magnetic particles can be dispersed by blocking a magnetic field by stopping the flow of electric current through the electromagnets. That is, fluctuations in magnetic field can be controlled by controlling the flow of electric current through the electromagnets. Such an embodiment that does not involve mechanical movement of the magnetism source can be appropriately implemented by those skilled in the art with reference to JP-A-2008-12490.

6. Fluorescence Detecting Means

A fluorescence detecting means is not particularly limited and can be easily selected by those skilled in the art. For example, a fluorescence detecting means shown in FIG. 4 comprises a light-generating unit 73, a camera (CCD camera) 72, a coaxial episcopic illumination system 75, and a personal computer (PC) 71. When the fluorescence detecting means is used, light generated by the light-generating unit 73 enters the coaxial episcopic illumination system 75 attached to the CCD camera 72 through a light cable 74 and passes through lenses in the coaxial episcopic illumination system 75 to illuminate a droplet 11 in a reaction container 4. An electric signal detected by the CCD camera is sent to the PC in real time, and therefore a change in the fluorescence intensity of the droplet can be monitored.

As the light-generating unit, an LED, a laser, a lamp, or the like can be used. Further, any light-receiving element can be used for detection without any limitation, and examples of such a light-receiving element range from cheap photodiodes to photomultiplier tubes designed for higher sensitivity. For example, in case of using SYBR (Registered Trade Mark) GREEN I, the dye specifically binds to double-stranded DNA and emits fluorescence at about 525 nm, and therefore light is detected by a light-receiving surface of the CCD camera by cutting off light other than light with an intended wavelength using a filter.

Fluorescence emitted from the droplet can be observed in a darkroom by irradiating, with exciting light, a point having a temperature at which an extension reaction by DNA polymerase occurs (usually about 68 to 74° C.) in a state where the droplet-stays at this point. Further, the melting curve of an amplified product can also be obtained and the droplet can be transferred by expanding an area irradiated with exciting light to irradiate an area from a point having a temperature at which thermal denaturation occurs to a point having a temperature at which annealing occurs.

7. Manipulation of Droplet and Magnetic Particles

[7-1. Encapsulation of Droplet]
[7-1-1. Method for Encapsulating Droplet by Adding the Droplet]

In case of using the droplet encapsulating medium having a melting point lower than a reaction temperature as described in the above [2-1], droplet encapsulation can be performed by, before the droplet reaction manipulation, adding a liquid for forming a droplet into a liquid material contained in a container by dropping or the like. When the resultant liquid material is exposed to a temperature equal to or lower than the melting point of the material, the encapsulated droplet can also be fixed.

In case of using the droplet encapsulating medium having a gel-sol transition point lower than a reaction temperature as described in the above [2-2], droplet encapsulation can be performed by, before the start of droplet manipulation, dissolving a gelling agent in a liquid material contained in a container to prepare a mixed liquid, adding a liquid for forming a droplet to the mixed liquid by dropping or the like, and then, cooling the mixed liquid to turn the liquid into a gel.

Droplet encapsulation can be performed also by, before the start of droplet manipulation, dropping a droplet into a sol-state droplet encapsulating medium, and then, exposing the droplet encapsulating medium to a temperature equal to or lower than sol-gel transition point thereof to turn the medium into a gel; or by directly injecting a water-based liquid into a gel-state droplet encapsulating medium by puncture.

The above methods make it possible to completely encapsulate or fix a droplet in a droplet encapsulating medium. Fixation of a droplet makes storage easy. For example, as shown in FIG. 1(a), encapsulated droplets 12, 13 and 14 may be placed on a transport path so as to come into contact with a transport surface 41 of the inner wall of a container 4.

Droplet encapsulation may be devised in the following manner. For example, as shown in FIG. 5(b), when a droplet encapsulating medium 3 is charged onto a thin bottom member 42 placed on a multi-well device 9 such as a multi-well, the bottom member is bent downward at portions located above the wells by the weight of the encapsulating medium 3 so that recessed portions are formed. By placing droplets 1 at the recessed portions, it is possible, even when the droplet encapsulating medium 3 still has flowability, to prevent the dropped droplets 1 from unintentionally moving. Further, it is also possible, when two or more droplets are encapsulated, to narrow the space between the droplets, which makes it possible to reduce the size of the container.

[7-1-2. Method for Encapsulating Droplet by Coalescing Droplet on Encapsulating Medium with Encapsulated Droplet]

When a water-based liquid containing one of elements required to construct a reaction system or a treatment system is placed on a transport path by the above-descried method and a water-based liquid containing the other element is placed in a droplet state on a gel-state droplet encapsulating medium, both the elements are mixed together in the following manner.

When a liquid is placed in a droplet state on a droplet encapsulating medium having no flowability (that is, a solid-state medium for encapsulating a droplet under a temperature condition equal to or lower than the melting point of the medium; or a gel-state medium for encapsulating a droplet under a temperature condition equal to or lower than the sol-gel transition point of the medium), as shown in, for example. FIG. 1(b), a liquid 2 can be placed in a recess formed in part of the upper surface of a droplet encapsulating medium 31 by pressing or trimming. By forming such a recess, it is possible to prevent the liquid 2 placed on the droplet encapsulating medium 31 from unintentionally spreading or moving. The depth D2 of the recess is not particularly limited. For example, the recess preferably has such a depth that the deepest portion of the recess does not reach a transport surface 41. The recess may have such a depth that the deepest portion of the recess does not reach the highest level of a droplet that has already been encapsulated so as to come into contact with the transport surface 41. More specifically, a depth D2 of about 1 mm is sometimes enough for the recess.

By exposing the droplet encapsulating medium to a temperature equal to or higher than sol-gel transition point thereof, the droplet encapsulating medium is turned into a sol having flowability, and therefore a droplet containing the other element sinks in the droplet encapsulating medium to the bottom surface of a container. The sunken droplet is coalesced with a droplet that contains the one of the elements and has already been encapsulated so that the one of the elements and the other element are mixed together and coexist in one encapsulated droplet. This makes it possible to put the one of the elements and the other element into a state where they can be subjected to a reaction or a treatment.

The droplet containing the other element and the droplet containing the one of the elements can be coalesced together by placing the droplet containing the other element just above the droplet containing the one of the elements that has already been encapsulated. Alternatively, when at least one of the droplet containing the one of the elements and the droplet containing the other element contains magnetic particles, both the droplets can be coalesced together by sinking the droplet containing the other element to the bottom surface of the container so that said droplet is placed in a position different from a position in which the droplet containing the one of the elements has already been encapsulated and then by moving the droplet containing magnetic particles by fluctuating a magnetic field.

Further, in case that a droplet encapsulating medium is in a gel-state, as shown in FIG. 2(a), in a state where the droplet encapsulating medium 31 remains gelled, magnetic particles 8 can be separated toward a transport surface 41 while a droplet 2 remains placed on a droplet encapsulating medium 31 by bringing a magnetism source (magnet) 61 close to a container 4 to generate a magnetic field in a direction from the transport surface 41 side to the droplet 2 on the droplet encapsulating medium 31. At this time, the magnetic particles 8 to be separated form an aggregate by magnetism, and the magnetic particles forming an aggregate are separated together with a material adsorbed thereto and a slight amount of liquid adhering to the surfaces thereof. In other words, a small droplet 11b shown in FIG. 2(b) containing the magnetic particles is separated from the droplet 2 shown in FIG. 2(a) regarded as a main droplet. The separated small droplet 11b is guided by the magnetic field and therefore can sink in the droplet encapsulating medium 31 to the transport surface 41 of the container while breaking the three-dimensional structure of the gel (FIG. 2(b)).

In such an embodiment, a specific example of the droplet placed on the droplet encapsulating medium may be a liquid composed of magnetic particles and a sample containing nucleic acid to be amplified. In this case, a small droplet is obtained in a state where the droplet contains the magnetic particles and a liquid composed of the sample containing nucleic acid adsorbed to the magnetic particles.

The sunken small droplet 11b is coalesced with the droplet 14 that contains the one of the elements and has already been encapsulated so that the one of the elements and the other element are mixed together and coexist in one encapsulated droplet 11c. This makes it possible to put the one of the elements and the other element into a state where they can be subjected to a nucleic acid amplification reaction or pretreatment therefor.

[7-2. Transfer of Encapsulated Droplet]
[7-2-1. Transfer of Droplet in Droplet Encapsulating Medium with Flowability]

A magnetic particle-containing droplet encapsulated in a droplet encapsulating medium having flowability (that is, a liquid-state medium for encapsulating a droplet under a temperature condition equal to or upper than the melting point of the medium; or a sol-state medium for encapsulating a droplet under a temperature condition equal to or upper than the sol-gel transition point of the medium), is transferred along a droplet transport path on the following principle. As shown in FIGS. 2(g) and 2(h), when a magnetic field is generated by bringing a magnet 61 close to a droplet 11g containing magnetic particles in a direction from a transport surface 11 of a container to the inside of the container and is then fluctuated by moving the magnetic field approximately parallel to the transport surface 41 of the container, the magnetic particles are concentrated in the droplet on the side toward which the magnet 61 is moved so that a force trying to transfer the entire droplet in the direction in which the magnet 61 is moved is exerted. As long as traction is transmitted to water constituting the droplet due to the hydrophilic surface of the magnetic particles used in the present invention when the magnetic particles are transferred along the droplet transport surface; and further the contact angle of the droplet on the substrate is sufficiently large; the surface roughness of the transport surface is sufficiently small; the kinetic viscosity of the droplet encapsulating medium and the initial velocity of movement of the magnetic field is suitable, it is possible to prevent the magnetic particles from overcoming the surface tension of the droplet and therefore to transfer the entire droplet without allowing the magnetic particles to come out of the droplet.

For example, when 3 μL of magnetic particle dispersion containing magnetic particles having a particle diameter of 1 μm in an amount of 500 μg in water is encapsulated in a droplet encapsulating medium to obtain a droplet, and a neodymium permanent magnet is brought close to the droplet from the outside of a container, under conditions where the contact angle of the droplet on a transport surface is 105° (deg) (at 25° C.), the surface roughness Pa of the transport surface is 0.1 μm, and the kinetic viscosity of the droplet encapsulating medium is 15 mm$^2$/s (at 25° C.), it is possible to prevent the magnetic particles from overcoming the surface tension of the droplet, that is, it is possible to transfer the entire droplet without allowing the magnetic particles to come out of the droplet as long as the magnet is moved at an initial velocity of 10 cm/sec or less. In this case, it is possible to transfer the entire droplet at a maximum velocity of 100 cm/sec.

Transfer of a droplet containing magnetic particles can be reproducibly performed by setting parameters such as the composition of a water-based liquid constituting the droplet, the particle diameter of the magnetic particles and the amount of the magnetic particles to be used, the contact angel of the droplet on a transport surface, the surface roughness of the transport surface, the kinetic viscosity of a droplet encapsulating medium, the strength of a magnetic field, and the rate at which the magnetic field is fluctuated. Those skilled in the art can adjust each of the parameters by checking the behavior of the magnetic particles contained in the droplet to perform the droplet transfer.

It is to be noted that in this embodiment, the volume of a droplet that can be transferred can be appropriately determined by those skilled in the art. For example, when 10 to 1,000 μg of magnetic particles are used, the volume of a droplet can be set to 0.05 μL to 5 μL.

[7-2-2. Transfer of Droplet in Gel-State Droplet Encapsulating Medium]

A gel-state droplet encapsulating medium has characteristics inherent to gel, and therefore an encapsulated droplet can be transferred even when the droplet encapsulating medium itself does not have flowability. A magnetic particle-containing droplet encapsulated in a gel-state droplet encapsulating medium can be transferred along a droplet transport path while breaking the three-dimensional structure of gel of the droplet encapsulating medium.

For example, when 3 fit of magnetic particle dispersion containing magnetic particles having a particle diameter of 3 μm in an amount of 500 μg in water is encapsulated in a droplet encapsulating medium to obtain a droplet, and a ferrite permanent magnet is brought close to the droplet from the outside of a container, under conditions where the contact angle of the droplet on a transport surface in the sol-state droplet encapsulating medium is 105° (deg) (at 25° C.), the surface roughness Ra of the transport surface is 0.1 μm, and the kinetic viscosity of the gel-state droplet encapsulating medium is 15 mm$^2$/s (at 25° C.), it is possible to transfer the entire droplet without allowing the magnetic particles to come out of the droplet as long as the magnet is moved at an initial velocity of 10 cm/sec or less. In this case, it is possible to transfer the entire droplet at a maximum velocity of 100 cm/sec.

In an embodiment in which a droplet is transferred in a gel-state droplet encapsulating medium, the volume of the droplet that is carried by magnetic particles is often as small as the volume of the droplet adhering to the surfaces of magnetic particles. For example, when magnetic particles are used in an amount of 100 to 500 μg, the volume of a droplet that is carried by the magnetic particles is only about 1 μL to 5 μL. This embodiment is suitable when the amount of a droplet carried together with magnetic particles is preferably as small as possible, such as when an intended component to be carried by magnetic particles is only the component adsorbed to the surfaces of the magnetic particles.

[7-2-3. Transfer on Temperature Variable Region]

As mentioned above, the embodiment in which an encapsulated droplet itself is transferred is preferably used when the liquid temperature of the encapsulated droplet needs to be changed. When a transport surface has a temperature variable region provided by creating a temperature gradient along a droplet transport path, the liquid temperature of an encapsulated droplet can be quickly and easily adjusted by transferring the encapsulated droplet itself to a point having a temperature required for treatment performed in a liquid constituting the encapsulated droplet.

Therefore, the present invention is useful, for example, when a nucleic acid amplification reaction requiring two or more temperature conditions having a relatively large difference is performed. For example, among the above-mentioned methods for nucleic acid amplification reaction, a PCR method, a LCR method, a TAS method, and the like are required to repeat a thermal cycle requiring two or three temperature conditions having a relatively large difference multiple times. According to the method of the present invention, as shown in FIGS. 2(g) and 2(h), an encapsulated droplet 11g composed of a reaction liquid for nucleic acid amplification containing the above-mentioned magnetic particles having hydrophilic surfaces, nucleic acid to be amplified, fluorochrome, and materials required for nucleic acid amplification reaction is transferred to a point having a temperature required for performing each of the steps of a nucleic acid amplification reaction by applying a fluctuating magnetic field to the droplet, and is allowed to stay at each of the point for necessary time. Therefore, complicated temperature conditions required for a nucleic acid amplification reaction can be easily achieved. Further, an amplified product can be appropriately detected by allowing a fluorochrome to be contained in at least a droplet encapsulating medium, which makes it possible to observe a nucleic acid amplification reaction performed in the droplet in real, time (real-time nucleic acid amplification).

Further, the present invention can be flexibly applied to a reaction or a treatment that may be selected by a user even when the reaction or treatment requires a wide range of temperature conditions. For example, an SDA method, a Qβ method, a NASBA method, an ICAN method, an ICAT method, an RCA method, and the like are methods for isothermal amplification reaction performed under one temperature condition in the range of about 37° C. to 65° C., but an optimum temperature differs depending on an object to be amplified. When the method according to the present invention is applied to any one of these nucleic acid amplification methods, desirable amplification efficiency can be achieved by simply placing a droplet at a point where the temperature of the droplet can be controlled at an optimum temperature for an object to be amplified.

[7-3. Separation of Magnetic Particles and Small Droplet Attached Thereto from Encapsulated Main Droplet]

[7-3-1. Separation of Small Droplet in Droplet Encapsulating Medium with Flowability]

A modification of the above-mentioned embodiment in which a droplet is transferred in a droplet encapsulating medium with flowability is embodiment in which the encapsulated droplet to be transferred is a small droplet separated from an another droplet regarded as a main (mother) droplet.

The another droplet is one encapsulated in the droplet encapsulating medium in the same container. In this embodiment, a magnetic field is applied to magnetic particles contained in the encapsulated another droplet to transfer the magnetic particles along a transport path so that the aggregated magnetic particles are drawn out of and separated from the main droplet without transferring the entire encapsulated main droplet. At this time, the separated aggregated magnetic particles convey around the surfaces thereof a material adsorbed thereto and a small amount of liquid (small droplet) derived from the main droplet.

For example, magnetic particles and a small droplet adhering thereto can be separated from a main droplet containing the magnetic particles by changing the above-mentioned various conditions allowing droplet transfer so that the amount of the magnetic particles contained is made relatively smaller in respect to a main droplet; the contact angle of the droplet on a transport surface is made relatively smaller; the surface roughness of the transport surface is made relatively larger; the kinetic viscosity of a droplet encapsulating medium is made relatively higher; or the initial velocity of fluctuation of a magnetic field is made relatively higher compared to each of the conditions for the droplet transfer. By significantly changing the conditions described above as examples, it is possible to increase the volume of the small droplet adhering to the magnetic particles. As in the case of the above-mentioned droplet transfer, separation of a small droplet can be performed by those skilled in the art by adjusting each of the parameters by checking the behavior of the magnetic particles contained in the droplet.

In this embodiment, the droplet encapsulating medium has flowability, and therefore the encapsulated main droplet itself is not fixed. For this reason, the droplet is more easily moved in the droplet encapsulating medium when the above-mentioned conditions are closer to the conditions for the transfer of the droplet itself, which tends to make it difficult to separate the magnetic particles and a small droplet adhering thereto from the main droplet. In this case, for example, a spot having an affinity for the droplet may be provided in part of the transport path on the transport surface. For example, by previously subjecting the spot to a treatment for relatively reducing water repellency, relatively increasing hydrophilicity, or relatively increasing surface roughness, it is possible to prevent the main droplet placed on the spot from unintentionally moving. Further, the similar effect can be obtained also by controlling an electric field by, for example, separately applying an unmoving magnetic field to the encapsulated main droplet in a desired position on a substrate from the bottom side of the substrate.

[7-3-2. Separation of Small Droplet in Gel-State Droplet Encapsulating Medium]

On the other hand, as shown in FIGS. 2(c) to 2(e), magnetic particles and a small droplet 11e adhering thereto can be separated also from a ma in droplet 11c containing the magnetic particles and encapsulated in a gel-state droplet encapsulating medium 31 while the droplet encapsulating medium 31 remains in a gel state having no flowability. This embodiment is based on the same principle as the embodiment shown in FIGS. 2(a) to 2(b) in which the magnetic particles and the small droplet 11b adhering thereto are separated from the main droplet 2 containing the magnetic particles and placed on the droplet encapsulating medium 31.

More specifically, the magnetic particles to be separated form an aggregate by magnetism, and the aggregated magnetic particles are separated together with a material adhered thereto and a small amount of liquid (FIG. 2(e)). In other words, the small droplet 11e containing the magnetic particles is separated from the encapsulated droplet 11e regarded as a main droplet. The separated small droplet 11e can be transferred along a transport path while breaking the three-dimensional structure of gel of the droplet encapsulating medium 31 under the guidance of a magnetic field. On the other hand, the encapsulated droplet whose volume is larger by a certain degree than the aggregated magnetic particles (i.e., the main droplet 11c) is fixed by the gel-state encapsulating medium and therefore cannot be displaced together with the aggregated magnetic particles. Therefore, the magnetic particles 8 are separated together with the small droplet 11e adhering thereto, but the main droplet stays in its initial position (FIGS. 2(d) and 2(e)). This makes it possible to very easily separate a small droplet containing magnetic particles from a main droplet without using a method (e.g., electric-field control) which may be used in the above-mentioned case using a droplet encapsulating medium having flowability to prevent an encapsulated droplet from unintentionally moving. For this reason, a gel-state droplet encapsulating medium has a very high degree of flexibility in the placement of a droplet, which makes it possible to flexibly determine a droplet transport path.

Further, as has been already described, in the embodiment in which a droplet is transferred in a gel-state droplet encapsulating medium, the volume of the droplet carried by magnetic particles is often as very small as that of the droplet adhering to the surfaces of the magnetic particles. Therefore, when a desired component to be carried by the magnetic particles is only the component adsorbed to the surfaces of the magnetic particles, the embodiment in which a small droplet is separated from a main droplet in a gel-state droplet encapsulating medium is preferred from the viewpoint of minimizing the amounts of extra liquid components carried by the magnetic particles to accurately separate the component adsorbed to the magnetic particles.

[7-4. Coalescence of Encapsulated Droplet Containing Magnetic Particles and Another Encapsulated Droplet]

A droplet containing magnetic particles can be coalesced with an another encapsulated droplet in the same container by exposure to a liquid constituting the another encapsulated droplet. A droplet encapsulating medium in which the another encapsulated droplet is encapsulated may be either with flowability or without flowability. By coalescing droplets together, mixing of components constituting the droplets, dissolution, or dilution can be performed.

In the present invention, a small droplet separated from an encapsulated main droplet composed of a liquid containing nucleic acid and magnetic particles by applying a fluctuating magnetic field can be coalesced with an another encapsulated droplet composed of a liquid in which a treatment such as a nucleic acid amplification reaction is performed. The another encapsulated droplet is, for example, a liquid composed of a nucleic acid extraction liquid, a liquid composed of a cleaning liquid, a liquid composed of a nucleic acid releasing liquid or the like.

For example, when a treatment for extracting nucleic acid is performed, a nucleic acid component contained in a small droplet 11b can be extracted by transferring the small droplet 11b containing magnetic particles and nucleic acid and other components adhering thereto in a droplet encapsulating medium 31 as shown in FIG. 2(b), and then coalescing the small droplet 11b with an another encapsulated droplet 14 composed of a nucleic acid extraction liquid (FIG. 2(c)). Further, as shown in FIGS. 2(d) and 2(e), by applying a fluctuating magnetic field, the magnetic particles are separated together with the extracted nucleic acid and a small droplet 11e adhering thereto from an encapsulated droplet 11c composed of the nucleic acid extraction liquid coalesced with the small droplet 11b, and are transferred in the droplet encapsulating medium 31.

A treatment for cleaning the magnetic particles can also be performed in the same manner. That is, the magnetic particles can be cleaned by transferring the another small droplet containing the magnetic particles and the nucleic acid adhering thereto in the encapsulating medium, and then coalescing the small droplet with an another encapsulated droplet composed of a cleaning liquid. By cleaning the magnetic particles, the nucleic acid adsorbed to the magnetic particles can be cleaned. Further, by applying a fluctuating magnetic field, the magnetic particles are separated together with the cleaned nucleic acid and a small droplet adhering thereto from the encapsulated droplet composed of the cleaning liquid, and are transferred in the encapsulating medium. A treatment for releasing the nucleic acid is also performed in the same manner.

A nucleic acid-containing sample or a small droplet that has been subjected to the above-mentioned nucleic acid extraction treatment, cleaning treatment, and/or nucleic acid releasing treatment if necessary is coalesced with a droplet composed of a reaction liquid for nucleic acid amplification (FIGS. 2(f) and 2(g)). This makes it possible to obtain a droplet 11g composed of the reaction liquid for nucleic acid amplification containing nucleic acid to be amplified and magnetic particles. A nucleic acid amplification reaction can be initiated by transferring the obtained droplet 11g to a point in the temperature variable region having a temperature at which a nucleic acid amplification reaction occurs (FIG. 2(h)).

As described above, a series of treatments including a nucleic acid amplification reaction and pretreatment therefor is performed in a perfect closed system. Further, these treatments can be easily performed by dispersing magnetic particles in an encapsulated droplet, aggregating the magnetic particles for transfer, and transferring the magnetic particles between droplets and between points having desired temperatures in a gel.

EXAMPLES

Example 1

As magnetic particles having hydrophilic surfaces, Magnetic Beads included as a constituent reagent in Plasmid DNA Purification Kit MagExtractor—Genome—kit available from TOYOBO Co., Ltd. (hereinafter, simply referred to as "magnetic silica beads") were used. The magnetic silica beads included in the kit were previously cleaned by repeating the following operation five times: the magnetic silica beads were suspended in pure water whose volume was ten times larger than that of an undiluted liquid containing the magnetic silica beads, and then the suspension was centrifuged at 500×g for 1 minute to remove supernatant. Then, the magnetic silica beads were suspended in pure water so that the amount of the magnetic silica beads contained in the pure water was adjusted to 100 mg (dry)/mL in terms of dry weight of the beads.

The composition of a reaction liquid for PCR was as follows: 50 mM potassium chloride, 10 mM Tris-HCl buffer (pH 9.5), 5 mM magnesium chloride, 0.6 µM PCR primer for β-actin detection (Forward) (manufactured by Applied Biosystems), 0.6 µM PCR primer for β-actin detection (Reverse) (manufactured by Applied Biosystems), and 0.75 U heat-resistant DNA polymerase (Ex Taq DNA Polymerase manufactured by TAKARA SHUZO CO., LTD.). Further, in order to prevent deactivation of the DNA polymerase caused by adsorption to the surface of a substrate, the magnetic particles, the interface with oil, etc., 0.1 weight % bovine serum albumin was added. To the reaction liquid for PCR were added 3 ng of purified standard human genomic DNA (manufactured by Roche) and the magnetic silica, beads so that the concentration of the magnetic silica beads was 10 μg/μL in terms of dry weight of the beads.

As a bottom member of a reaction container, a 2.8 μm-thick polypropylene film (ALPHAN EM-501K manufactured by Oji Specialty Paper Co., Ltd.) was used, and a silicone oil (KF-56 manufactured by Shin-Etsu Chemical Co., Ltd.) was filled into the reaction container.

SYBR® GREEN I manufactured by Invitrogen was added to a droplet composed of the reaction liquid for PCR so as to be diluted to a concentration 10,000 times smaller than that of its undiluted liquid product. Further, SYBR® GREEN I was added to the silicone oil so as to be diluted to a concentration 50,000 times smaller than that of its undiluted liquid product.

Figure 3:
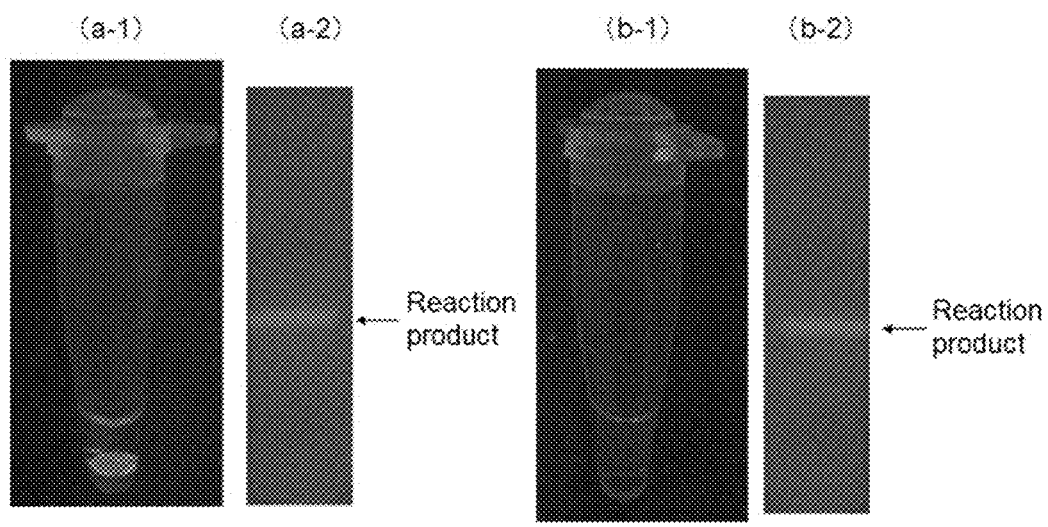
FIG. 3 shows images obtained in Example 1 by observing fluorescence by ultraviolet irradiation after the completion of a PCR reaction when a fluorochrome was added to silicone oil (a-1) and when a fluorochrome was not added (b-1).

When a gene amplified product is produced, fluorescence emitted when the fluorochrome binds to double-stranded DNA is observed. The results of a PCR reaction performed according to this example are shown in FIG. 3. FIG. 3(*a-1*) is an image obtained by observing fluorescence of SYBR® GREEN I by ultraviolet irradiation after the completion of PCR when the fluorochrome was added to the silicone oil and FIG. 3(*b-1*) is an image obtained by observing fluorescence of SYBR® GREEN I by ultraviolet irradiation after the completion of PCR when the fluorochrome was not added to the silicone oil. Only when the fluorochrome was added to the silicone oil (a-1), a signal was observed from the droplet collected in a polypropylene tube by ultraviolet irradiation. This signal was observed as yellow-green fluorescence having a wavelength of 472 nm derived from SYBR® GREEN I. On the other hand, gene amplification occurred also in (b-1), but fluorescence was hardly observed.

It is to be noted that the results of agarose-gel electrophoresis of the gene amplified products obtained in (a-1) and (b-1) are shown in FIGS. 3(*a-2*) and 3(*b-2*), respectively. As shown in FIGS. 3(*a-2*) and 3(*b-2*), in both cases, the gene amplification reaction was normally completed.

Example 2

PCR was performed in the same manner as in Example 1 except that each of fluorochromes, SYBR-Green I, YO PRO-1, and SYTO-13 (all of which are manufactured by Invitrogen) were used and that the concentration of each of the fluorochromes contained in the droplet and the concentration of each of the fluorochromes contained in the oil were varied. Differences between the intensity of fluorescence observed before the start of PCR and the intensity of fluorescence observed after the start of PCR are shown in Tables 1 to 3. Table 1 shows results obtained using SYBR-Green I, Table 2 shows results obtained using YO PRO-1, and Table 3 shows results obtained using SYTO-13.

It is to be noted that all the droplets had a volume of 3 μL, and the composition of the reaction liquid was as follows: 25 mM Tris-HCl (pH 8.3), 8 mM $MgCl_2$, 0.2% (w/v) bovine serum albumin, 0.125 U/μL Ex Taq DNA polymerase (manufactured by TAKARA BIO INC.), 250 μM dNTP, and primers for human β-actin gene detection (each 1 μM).

One of the primers for human β-actin gene detection has a sequence of 5'-CATCGAGCACGGCATCGTCACCAA-3' (SEQ ID No. 1) and the other primer for human β-actin gene detection has a sequence of 5'-GCGGGCCACTCACCTGGGTCATCT-3' (SEQ ID No. 2).

To the droplet of 3 μL, 510 μg of magnetic beads (MagExtractor®—Plasmid—manufactured by TOYOBO Co., Ltd.) were added. As a droplet encapsulating medium, a silicone oil KF-56 manufactured by Shin-Etsu Chemical Co. Ltd. was used. PCR was performed under conditions described in T. Ohashi, H. Kayama, N. Hanafusa, and Y. Togawa: Biomed. Microdevices, 9, 695 (2007). More specifically, one PCR cycle consisting of thermal denaturation (95° C., 0.5 sec), annealing (60° C., 1 sec), and extension (72° C., 5 sec) was repeated 40 times in total. The PCR cycle was performed by transferring the droplet composed of the reaction liquid containing the magnetic beads by moving the magnet provided outside the container and located just below the droplet at a rate of 1.1 cm/sec between a spot having a temperature of 95° C. and a spot having a temperature of 60° C. provided by creating a temperature gradient.

The fluorescence intensity of the droplet was measured using a cooled CCD camera (ST-402ME manufactured by SBIG) by taking an image from directly above the droplet in the oil with exposure for 5 seconds at maximum sensitivity. An exciting light source was a 470 nm blue LED, an exciting light-side band-pass filter was a 475 nm/40 nm band-pass filter, and a detection-side band-pass filter was a 535 nm/45 nm band-pass filter. Image analysis software Image J was used to calculate the amount of fluorescence of the entire droplet as a relative fluorescence intensity, and a value obtained by subtracting a fluorescence intensity measured before PCR (i.e., background) from a fluorescence intensity measured after PCR was defined as a data value. It has been found that, in this reference example, the optimum concentration of each of the fluorochromes in the droplet is in the range of about 0.5 to 2 μM and the optimum concentration of each of the fluorochromes in the oil is in the range of about 0.05 to 0.1 μM. When the fluorochrome was not previously added to the oil, a significant increase in fluorescence intensity was not detected. On the other hand, it has been found that fluorescence of amplified nucleic acid can be detected without adding the fluorochrome to the droplet as long as the fluorochrome is previously present in at least the oil.

TABLE 1

SYBR Green I

| | | Concentration of Fluolochrome in Droplet (μM) | | | | | |
|---|---|---|---|---|---|---|---|
| | | 0 | 0.5 | 1 | 2 | 5 | 10 | 20 |
| Concentration of Fluolochrome in Oil (μM) | 0 | 0 | −18 | −34 | −89 | −145 | −278 | −450 |
| | 0.01 | 46 | 32 | −9 | −25 | −89 | −123 | −241 |
| | 0.02 | 78 | 90 | 35 | −6 | −34 | −89 | −178 |
| | 0.05 | 156 | 178 | 202 | 78 | 12 | −10 | −66 |
| | 0.1 | 267 | 345 | 356 | 207 | 67 | 20 | −33 |
| | 0.2 | 176 | 150 | 89 | 67 | 34 | 22 | 17 |
| | 0.5 | 124 | 103 | 60 | 23 | 9 | −22 | −7 |

Data Value Unit: RFU (Relative fluorescent Unit)

TABLE 2

YO PRO-1

| | | Concentration of Fluolochrome in Droplet (μM) | | | | | |
|---|---|---|---|---|---|---|---|
| | | 0 | 0.5 | 1 | 2 | 5 | 10 | 20 |
| Concentration of Fluolochrome in Oil (μM) | 0 | 0 | 7 | 11 | 4 | −23 | −189 | −356 |
| | 0.01 | 70 | 123 | 167 | 203 | 170 | −45 | −177 |
| | 0.02 | 127 | 234 | 321 | 345 | 124 | −21 | −123 |
| | 0.05 | 280 | 340 | 450 | 521 | 278 | 29 | −78 |
| | 0.1 | 329 | 452 | 389 | 179 | 88 | −19 | −23 |
| | 0.2 | 256 | 498 | 367 | 98 | 7 | −7 | −6 |
| | 0.5 | 224 | 309 | 51 | 18 | −5 | 0 | −3 |

Data Value Unit: RFU (Relative fluorescent Unit)

TABLE 3

SYTO-13

| | | Concentration of Fluolochrome in Droplet (μM) | | | | | | |
|---|---|---|---|---|---|---|---|---|
| | | 0 | 0.5 | 1 | 2 | 5 | 10 | 20 |
| Concentration of Fluolochrome in Oil (μM) | 0 | 0 | -13 | -24 | -45 | -89 | -135 | -240 |
| | 0.01 | 45 | 34 | 37 | 67 | 37 | -50 | -169 |
| | 0.02 | 67 | 55 | 65 | 91 | 67 | 6 | -89 |
| | 0.05 | 89 | 80 | 103 | 85 | 67 | 13 | -16 |
| | 0.1 | 82 | 56 | 45 | 67 | 40 | -5 | 9 |
| | 0.2 | 67 | 34 | 39 | 30 | 19 | 2 | -6 |
| | 0.5 | 46 | 24 | 30 | 17 | 7 | -2 | 1 |

Data Value Unit: RFU (Relative fluorescent Unit)

The invention claimed is:

1. A real-time nucleic acid amplification reaction method for performing a nucleic acid amplification reaction in a droplet present in a container,
   wherein the droplet is composed of a nucleic acid amplification reaction liquid including a nucleic acid to be amplified and magnetic particles;
   the container holds a droplet encapsulating medium, and has a transport surface having a temperature gradient;
   the droplet encapsulating medium is insoluble or poorly soluble in the nucleic acid amplification reaction liquid; and
   a fluorochrome is initially added in the droplet encapsulating medium at the start of the nucleic acid amplification reaction,
   the method comprising transporting the droplet together with the magnetic particles by generating a magnetic field by means for applying a magnetic field to start and maintain a nucleic acid amplification reaction so that the droplet is placed on the transport surface at a temperature point at which the nucleic acid synthesis reaction is started and maintained, thereby controlling a temperature of the nucleic acid amplification reaction liquid.

2. The method according to claim 1, wherein 0.01 to 0.5 μM of fluorochrome is initially added in the droplet encapsulating medium at the start of the nucleic acid amplification reaction.

3. The method according to claim 1, wherein 0 to 20 μM of fluorochrome is initially added in the droplet at the start of the nucleic acid amplification reaction.

4. The method according to claim 1, wherein the droplet encapsulating medium has a gel-sol transition point lower than the temperature at which the nucleic acid amplification reaction is started and the temperature at which the nucleic, acid amplification reaction is maintained:
   the droplet encapsulating medium is in a gel state at the temperature point where the droplet is present before the start of the nucleic acid amplification reaction; and
   the droplet encapsulating medium is in a sol state at the temperature point where the droplet is present when the nucleic acid amplification reaction is started and maintained.

5. The method according to claim 1, wherein the droplet encapsulating medium has a melting temperature lower than the temperature at which the nucleic acid amplification reaction is started and the temperature at which the nucleic, acid amplification reaction is maintained;
   the droplet encapsulating, medium is in a solid-state before the start of the nucleic, acid amplification reaction, and
   the droplet encapsulating medium is in a melt-state when the nucleic acid amplification reaction is started and maintained.

6. The method according to claim 1, wherein the nucleic acid to be amplified and the magnetic particles is obtained, before the start of the nucleic acid amplification reaction, by bringing a nucleic acid-containing sample into contact with a nucleic acid extraction liquid in the presence of the magnetic particles in a droplet which is composed of the nucleic, acid extraction liquid and is present in the container in a position different from a position in which the droplet composed of the nucleic acid amplification reaction liquid is present, thereby adsorbing an extracted nucleic acid to the magnetic particles, and
   wherein the magnetic particles and the extracted nucleic acid are transported by transfer of the magnetic particles from the nucleic acid extraction liquid into the nucleic acid amplification reaction liquid.

7. The method according to claim 6, wherein the magnetic particles and the extracted nucleic acid are cleaned in a droplet which is composed of a cleaning liquid and is present in the container in a position different from positions in which the droplet composed of the nucleic acid amplification reaction liquid and the droplet composed of the nucleic acid extraction liquid are present, and then are transported by transfer of the magnetic particles from the droplet composed of the cleaning liquid into the nucleic acid amplification reaction liquid.

8. The method according to claim 6, wherein the magnetic particles and the extracted nucleic acid are exposed to a droplet which is composed of a nucleic acid releasing liquid and is present in the container in a position different from positions in which the droplet composed of the nucleic acid amplification reaction liquid and the droplet composed of the nucleic acid extraction liquid are present, and then are transported by transfer of the magnetic particles from the droplet: composed of the nucleic acid releasing liquid into the nucleic acid amplification reaction liquid.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial
<220> FEATURE:
<223> OTHER INFORMATION: synthetic primer

<400> SEQUENCE: 1
catcgagcac ggcatcgtca ccaa                                    24

<210> SEQ ID NO 2
<211> LENGTH: 24
<212> TYPE: DNA
<213> ORGANISM: Artificial
<220> FEATURE:
<223> OTHER INFORMATION: synthetic primer

<400> SEQUENCE: 2
gcgggccact cacctgggtc atct                                    24